(12) United States Patent
Sirianni

(10) Patent No.: US 11,504,482 B2
(45) Date of Patent: Nov. 22, 2022

(54) PRECISION STEERABLE AND ANGLED MEDICATION DELIVERY SYSTEM

(71) Applicant: Peter A. Sirianni, Tyler, TX (US)

(72) Inventor: Peter A. Sirianni, Tyler, TX (US)

( * ) Notice: Subject to any disclaimer, the term of this patent is extended or adjusted under 35 U.S.C. 154(b) by 273 days.

(21) Appl. No.: 15/916,063

(22) Filed: Mar. 8, 2018

(65) Prior Publication Data
US 2018/0256828 A1 Sep. 13, 2018

Related U.S. Application Data

(60) Provisional application No. 62/468,870, filed on Mar. 8, 2017.

(51) Int. Cl.
| | |
|---|---|
| *A61M 5/32* | (2006.01) |
| *A61M 5/315* | (2006.01) |
| *A61M 5/31* | (2006.01) |
| *A61M 5/34* | (2006.01) |

(52) U.S. Cl.
CPC ........ *A61M 5/3287* (2013.01); *A61M 5/3137* (2013.01); *A61M 5/31511* (2013.01); *A61M 5/34* (2013.01); *A61M 5/345* (2013.01); *A61M 2005/3139* (2013.01); *A61M 2005/341* (2013.01)

(58) Field of Classification Search
CPC ...... A61M 2005/341; A61M 2005/342; A61M 5/34; A61M 2005/3289; A61M 5/32; A61M 2210/0637; A61M 5/3287; A61M 5/3137; A61M 5/31511; A61M 5/345; A61C 5/40; A61C 5/50; A61C 19/06; A61C 19/063; A61C 17/02; A61C 17/024; A61C 17/028; A61C 17/14
See application file for complete search history.

(56) References Cited

U.S. PATENT DOCUMENTS

| | | | |
|---|---|---|---|
| 762,603 A | | 6/1904 | Witkowski |
| 1,125,887 A | * | 1/1915 | Schimmel ............... A61M 5/32 604/117 |
| 1,569,961 A | * | 1/1926 | Bauchert ............... A61M 5/347 604/241 |
| 2,748,768 A | * | 6/1956 | Lipari ..................... A61M 5/28 604/193 |
| 3,118,447 A | * | 1/1964 | Hunt .................. A61M 5/31511 604/227 |

(Continued)

FOREIGN PATENT DOCUMENTS

WO WO-2017062935 A1 * 4/2017 ............. A61M 5/34

OTHER PUBLICATIONS

PCT Patent Application No. PCT/US2018/021602 International Search Report and Written Opinion dated Jun. 28, 2018.

*Primary Examiner* — Nilay J Shah
(74) *Attorney, Agent, or Firm* — Foley & Lardner LLP

(57) ABSTRACT

A precision steerable and angled medication delivery system is disclosed. The system may direct a delivery mechanism in connection with a control syringe to delivery sites within a patient's body. In this manner, therapeutic injections may be performed at precise locations as desired. The precision steerable and angled medication delivery system may have a structure configured to orient at least a portion of an elongate penetrative feature such as needle to be at least partially non-parallel to a longitudinal axis, further facilitating performance of therapeutic injections at precise locations.

40 Claims, 36 Drawing Sheets

(56) References Cited

U.S. PATENT DOCUMENTS

| | | | | |
|---|---|---|---|---|
| 4,250,881 | A | | 2/1981 | Smith |
| 4,444,560 | A | * | 4/1984 | Jacklich ............ A61M 5/31581 604/224 |
| 4,512,769 | A | * | 4/1985 | Kozam ................. A61M 3/005 604/209 |
| 4,581,022 | A | * | 4/1986 | Leonard ............ A61M 5/31581 222/391 |
| 5,284,476 | A | | 2/1994 | Koch |
| 5,514,113 | A | | 5/1996 | Anderson et al. |
| 5,628,734 | A | | 5/1997 | Hatfalvi |
| 5,876,384 | A | * | 3/1999 | Dragan .................. A61M 1/84 604/264 |
| 5,964,740 | A | * | 10/1999 | Ouchi ............... A61M 25/0084 604/164.01 |
| 6,079,979 | A | * | 6/2000 | Riitano ................. A61C 17/02 433/224 |
| 6,258,067 | B1 | | 7/2001 | Hill |
| 6,394,984 | B1 | | 5/2002 | Hill |
| 6,494,713 | B1 | * | 12/2002 | Pond ........................ A61C 5/40 433/224 |
| 7,481,816 | B2 | | 1/2009 | Richter et al. |
| 7,875,007 | B2 | | 1/2011 | Perot et al. |
| RE44,509 | E | | 9/2013 | Pond |
| 8,603,028 | B2 | | 12/2013 | Mudd et al. |
| 8,758,300 | B2 | | 6/2014 | Bakhtyari-Nejad-Esfahani |
| 9,186,247 | B2 | | 11/2015 | Nyte |
| 2003/0161824 | A1 | | 8/2003 | Rackley et al. |
| 2008/0058717 | A1 | * | 3/2008 | Spector .................... A61C 5/62 604/117 |
| 2012/0253294 | A1 | * | 10/2012 | Nyte .................... A61M 5/329 604/239 |
| 2013/0149664 | A1 | | 6/2013 | San Miguel |
| 2014/0066845 | A1 | | 3/2014 | Mudd et al. |
| 2014/0249411 | A1 | | 9/2014 | Li et al. |
| 2014/0276622 | A1 | | 9/2014 | Racz |
| 2015/0112278 | A1 | | 4/2015 | Ray et al. |
| 2016/0095985 | A1 | | 4/2016 | Novak |

* cited by examiner

LATERAL/LONGITUDINAL TRANSLATION, YAW

PITCH, ELEVATION

LONGITUDINAL AXIAL ROLL

ARTICULABLE IN 6 DEGREES OF FREEDOM

PRECISION STEERABLE AND ANGLED MEDICATION DELIVERY SYSTEM

CROSS-REFERENCE TO RELATED APPLICATIONS

This application claims priority to, and the benefit of, U.S. Provisional Patent Application Ser. No. 62/468,870, entitled "STEERABLE MEDICATION DELIVERY SYSTEM," filed Mar. 8, 2017, the contents of which are incorporated herein by reference in their entirety for all purposes.

TECHNICAL FIELD

This disclosure relates to a medication delivery system, and more particularly, a precision steerable and angled medication delivery system.

BACKGROUND

Injection providers frequently desire to provide patients with injections of medication. However, the delivery target for the medication may be located deep within the body and/or may be surrounded by obstacles, such as blood vessels, nerves, bones, tissue, spinal structures, and the like. Furthermore, tumors may provide unexpected or unusual obstacles. In further instances, patient comfort may render accurate placement critical and diminish available time for needle insertion, medication injection, and needle removal.

Traditionally, needles have been guided along a linear path by an injection provider, directly impinging then traveling through a patient's skin. However, such guidance is prone to inaccuracy, similar to the inaccuracy experienced by one attempting to write a sentence by grasping a pencil from the eraser end and projecting it outwardly from the fingertips, with the arm elevated from the writing surface. Such inaccuracy exacerbates risk of injury to the patient and diminishes the precision of guidance of the injection. Moreover, such linear motion precludes steering around obstacles to the delivery target.

SUMMARY

A precision steerable and angled medication delivery system is disclosed. The precision steerable and angled medication delivery system includes a delivery mechanism that includes a control syringe attachment configured to couple to a delivery mechanism attachment of a control syringe, and a semi-rigid channel orientation structure. The semi-rigid channel orientation structure includes an arcuate portion, and a distal linear portion extending outwardly from the arcuate portion having a bend angle measured relative a syringe longitudinal axis of the control syringe.

A variable bend connector orientation structure is disclosed. The structure may include a control syringe attachable portion configured to connect to a delivery mechanism attachment of a control syringe and extend outwardly away from the control syringe, a fluid tight hinge, and a delivery mechanism attachment portion. In various embodiments, the fluid tight hinge joins the delivery mechanism attachable portion to the control syringe attachable portion, the fluid tight hinge translates the delivery mechanism attachable portion along an arcuate articulation path, and an articulation angle may be selectably fixed between the delivery mechanism attachable portion and the control syringe attachable portion.

A fixed bend connector orientation structure is disclosed. The structure may include a bent connector body connected to the delivery mechanism attachment of the control syringe and establishing a fixed bend angle between a longitudinal axis of a distal end of the bent connector body and a syringe longitudinal axis of the control syringe.

A control syringe is disclosed. The control syringe may include an integral syringe channel orientation structure extending from a distal end of the control syringe, wherein the integral syringe channel orientation structure is connectable to a delivery mechanism including a needle, and wherein the integral syringe channel orientation structure includes an angled delivery mechanism attachment configured to orient the needle at a syringe bend angle relative to a syringe longitudinal axis of the control syringe.

A rotatable connector orientation structure is disclosed. The rotatable connector orientation structure may include a main body having a main body central longitudinal axis and extending outwardly away from a control syringe and including a control syringe attachable portion configured to connect to a delivery mechanism attachment of the control syringe. The rotatable connector orientation structure may also include a rotatable body connectable to a control syringe attachment of a delivery mechanism and a position setting interface interstitially disposed between the rotatable body and main body and including a first surface that is a mesial face of the rotatable body relative to the main body and a second surface that is a mesial face of the main body relative to the rotatable body. In various embodiments, the first and second faces are frictionally interlocked by conjugate serrations. The rotatable body may have a rotatable body orientation axis extending form the center of the rotatable body and forming a rotation angle relative to the main body central longitudinal axis.

A precision steerable and angled medication delivery system is disclosed. The precision steerable and angled medication delivery system may include a control syringe having a longitudinal axis and configured to contain a reservoir of medication, a delivery mechanism in fluid communication with the control syringe and having an elongate penetrative feature configured to penetrate a patient's skin to permit subcutaneous delivery of the medication, and an orientation structure configured to orient at least a portion of the elongate penetrative feature to be at least partially non-parallel to the longitudinal axis.

A method of directionally controlled medication delivery is disclosed. The method may include removing a stylette from a delivery mechanism, setting aside a stylette from a delivery mechanism, attaching a delivery mechanism to a control syringe, loading a control syringe with a fluid, forming an orientation structure, inserting a delivery mechanism into a patient skin at an entry point, guiding the delivery mechanism around an obstacle and through intervening tissue to a delivery site, and delivering a medication to a delivery site.

A method of delivery mechanism guidance is disclosed. The method may include forming an anchoring pivot, constraining, by the anchoring pivot, translational motion in at least one degree of freedom, and converting a single direction angular motion of a control syringe into a two direction linear translation of the delivery mechanism. The method may further include bending the delivery mechanism and directing the delivery mechanism along a curved path through a tissue.

A fixed bend connector orientation structure is provided. The fixed bend connector orientation structure may include a control syringe attachable portion configured to connect to a delivery mechanism attachment of a control syringe and extend outwardly away from the control syringe. The fixed bend connector orientation structure may include a delivery mechanism attachable portion configured to attach to a delivery mechanism including a needle. The fixed bend connector orientation structure may further include a bent connector body extending between the control syringe attachable portion and the delivery mechanism attachable portion and establishing a fixed bend angle between a longitudinal axis of a distal end of the bent connector body and a syringe longitudinal axis of a control syringe attachable portion configured to attach to the control syringe.

In one embodiment, the fixed bend connector may be provided at an angle so that the needle resides at or about 90 degrees from the longitudinal axis of the syringe. Of course, any desired angle may be provided. In still other embodiments, the fixed bend connector may have an adjustable or selectable angle such that the needle may be provided at a desired angle relative to the longitudinal axis of the control syringe when assembled and in use.

DESCRIPTION OF THE FIGURES

Like elements are referenced with like numerals.

DETAILED DESCRIPTION

Figure 1:
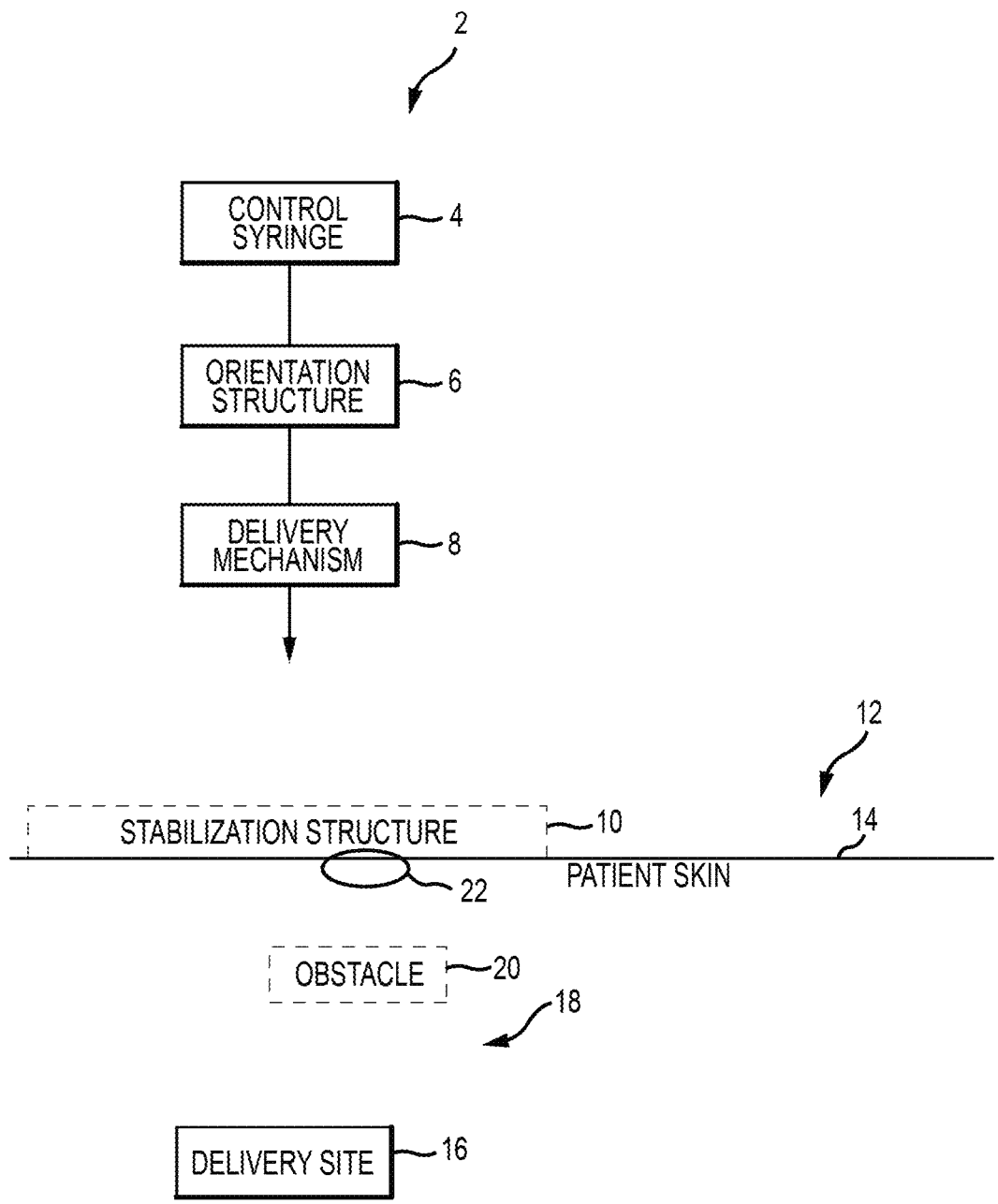
FIG. 1 depicts a block diagram of various aspects of a precision steerable and angled medication delivery system.
Figure 2:
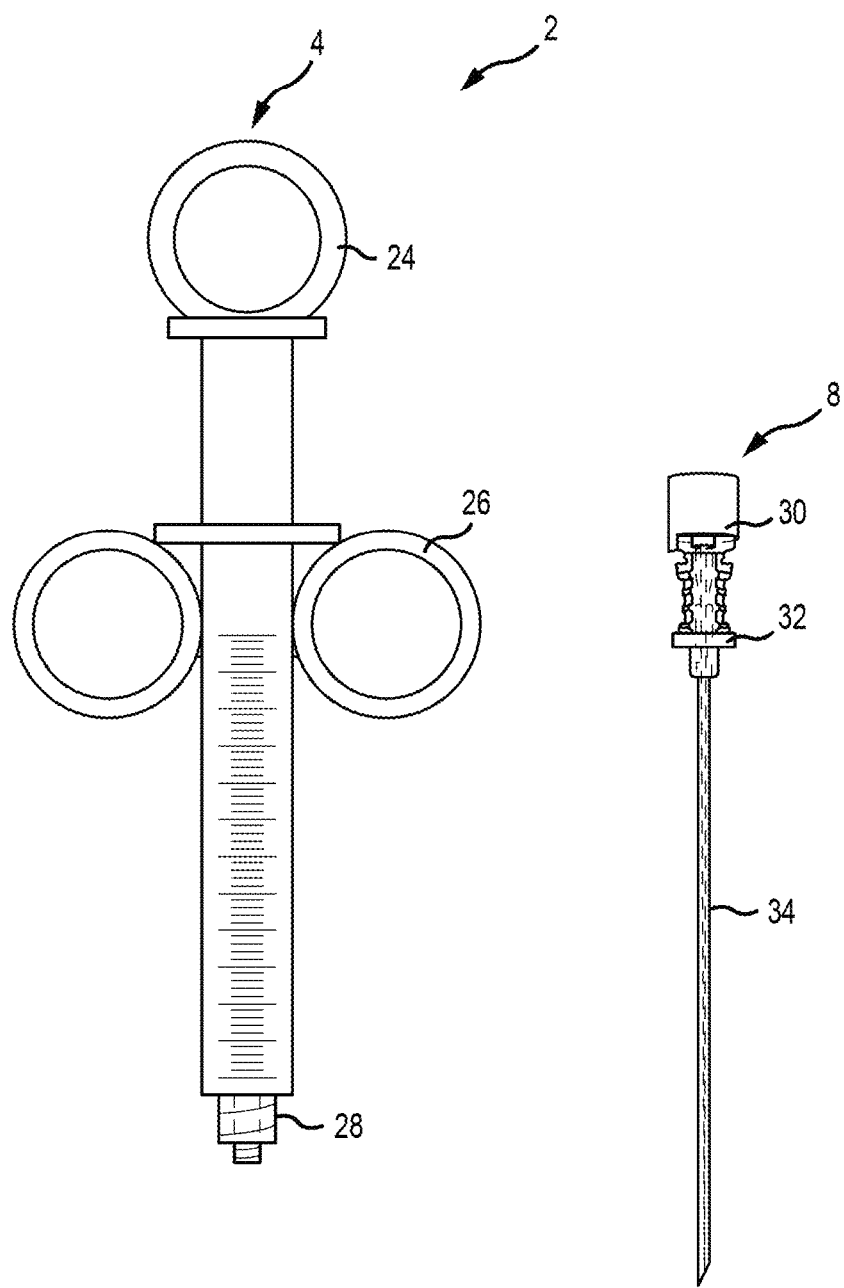
FIGS. 2-6 depict an example embodiment of a precision steerable and angled medication delivery system implementing a semi-rigid channel orientation structure at various stages of assembly and configuration.

Referring to FIG. 1, frequently injection providers provide therapeutic injections to patients 12, such as human patients, whether one's self or another, or such as animals. However, in many instances, a high degree of precision and a high degree of accuracy are desired when placing both the entry point 22 into the patient's skin 14, and also in directing the delivery mechanism 8 such as a needle through intervening tissue 18, around obstacles 20, and into a delivery site 16. For instance, there may be a desire to inject a pain relieving agent deep within the body and proximate to other bodily structures. In further instances, there may be a need to inject a vaccine and/or other medication. For instance, it may be desired to navigate a needle between vertebrae, into a feature of an eyeball, around a hematoma, or near to, but not interfering with nerves, or blood vessels or the like. An injection provider may wish to navigate the needle around an obstacle blocking a direct path from skin to the desired injection site. For instance, there may be a desire to locate an injection on an opposite side of a tumor, or an opposite side of a bone, or even an opposite side of an organ. In further instances, a vaccine injection or other injection may be desired to be performed in an arm, with the injection provider standing behind the patient such as out of sight, for instance, to ameliorate patient apprehensions. In such instances, a precision steerable and angled medication delivery system 2 and method are desirable.

A precision steerable and angled medication delivery system 2 may comprise a medication source, for instance, a syringe, such as a control syringe 4. A precision steerable and angled medication delivery system 2 may comprise a delivery mechanism 8. A control syringe 4 may contain a reservoir of medication. The delivery mechanism 8 may be in fluid communication with the control syringe 4 and may comprise a penetrative feature configured to penetrate a patient's skin 14 to permit subcutaneous delivery of the medication.

For example and with reference to FIGS. 1-25C, the delivery mechanism 8 may comprise a needle 34 configured to penetrate a patient's skin 14. The needle 34 may be a hollow needle in fluidic and mechanical communication with the control syringe 4. A stylette 30 may be disposable within the needle 34 to preserve a fluidic channel through the needle 34 until near the time of use. A control syringe attachment 32 may be integrally formed to or otherwise affixed to the needle 34 to facilitate mechanical joining of the delivery mechanism 8 to at least one of an orientation structure 6 and/or a control syringe 4, as will be discussed further herein. Thus, a delivery mechanism 8 may comprise a control syringe attachment 32 coupled to the delivery mechanism attachment 28 of a control syringe 4. The precision steerable and angled medication delivery system 2 may further include an orientation structure 6. An orientation structure 6 may permit the controllable orientation of the delivery mechanism 8 relative to the control syringe 4. For instance, while in many traditional scenarios a needle extends longitudinally from the end of a syringe for a common injection, in a directionally controlled medication delivery scenario, there may be an advantage associated with directionally control of the relationship of the delivery mechanism 8 to the control syringe 4. For example, in various embodiments, it may be desirable to permit angling of the delivery mechanism 8 relative to the control syringe 4.

The needle 34 may be selected from a variety of lengths and gauges. Furthermore, kits of a variety of embodiments of delivery mechanisms 8 discussed herein may be provided having needles 34 of different sizes and/or having delivery mechanisms 8 associated with different angles relative to the control syringe 4. For example 1.5" (38.1 mm) or 2.5" (63.5 mm) or 3.5" (88.9 mm) or 4" (101.6 mm) or 5" (127 mm) or 6" (152.4 mm) or any length as desired. In further embodiments, further sizes may be contemplated.

Thus, there may exist a precision steerable and angled medication delivery system 2 comprising a control syringe 4 having a longitudinal axis 3 and configured to contain a reservoir of medication. In further embodiments, the control syringe 4 may comprise one or more bends. For instance, the control syringe 4 may have an arcuate axis. Furthermore, the control syringe 4 may have a local bend at one or more locations. The precision steerable and angled medication delivery system 2 may also have a delivery mechanism 8 in fluid communication with the control syringe 4 and having an elongate penetrative feature (e.g., needle 34) configured to penetrate a patient's skin 14 to permit subcutaneous delivery of the medication to a delivery site 16. The precision steerable and angled medication delivery system 2 may also have an orientation structure 6 configured to orient at least a portion of the elongate penetrative feature such as needle 34 to be at least partially non-parallel to the longitudinal axis 3. In various embodiments, the orientation structure 6 is unitarily formed with the elongate penetrative feature such as needle 34 and/or the control syringe 4, such as comprising a portion of the elongate penetrative feature or a portion of the control syringe 4, and in further embodiments, it is distinct from the elongate penetrative feature such as needle 34 and/or control syringe 4 but attachable thereto, whether permanently or selectably attachable.

In conjunction with a precision steerable and angled medication delivery system 2, a stabilization structure 10, as shown in FIGS. 1, 7, 8, 14, and 15, may be implemented. A stabilization structure 10 may comprise a needle driver, or forceps, or pliers, or clamp, or any other mechanism whereby the orientation, rate of penetration, depth of penetration, acceleration, and stability of the delivery mechanism 8 may be controlled by the injection provider. For example, a needle driver may corral or may grip a portion of the delivery mechanism 8 to enhance fine control of the delivery mechanism 8 during use.

In various embodiments, a control syringe 4 may comprise a syringe having ring apertures disposed on a plunger and the syringe body configured to facilitate gripping and control of the positive and negative fluid pressure exerted by the plunger on the medication within the reservoir of the syringe body. For instance, with reference to FIGS. 1 and 2, a control syringe 4 may have a longitudinal axis 3. The control syringe 4 may comprise a bidirectional control plunger 24, comprising a syringe plunger with a ring configured to receive a user's thumb, a grip 26 configured to receive two of a user's fingers whereby a fluid retained within the control syringe 4 is controllably dispensed, and a delivery mechanism attachment 28 (see also FIG. 5) to attach the delivery mechanism 8 through which the fluid is dispensed. While reference is made herein to a "ring" and "ring aperture" and more broadly to a "grip," in various embodiments, a control syringe may alternatively or in addition, have detents, or open U-shaped structures, or magnetic features configured to interact with a provider's gloves, or any other structure or combination of structures, or with a robotic machine such as for telemedicine, as desired and whereby the translation of the plunger may be controlled in at least one or two directions.

A bidirectional control plunger 24 may be controllably translated (e.g., slidable) by a user's hand so that positive and negative pressure is selectably exertable on the fluid in the needle 34. Positive pressure may be exerted to prevent the needle 34 from clogging with patient skin during use. By incorporating a ring aperture comprising an annulus defining an aperture through a distal end of the bidirectional control plunger 24, the bidirectional control plunger 24 enables an injection provider to easily push and pull the plunger in either direction, without regripping, or repositioning the hand or control syringe 4, so that the magnitude of the exerted pressure is easily adjustable in small increments. Thus, the fine control over accurate and precise positioning of the precision steerable and angled medication delivery system 2 is enhanced and incidental tissue irritation or damage from unnecessary manipulation may be minimized.

A grip 26 may comprise a series of ring apertures comprising annuluses defining apertures through aspects of the control syringe 4. Such a grip 26 facilitates ready grasping and manipulation by fingers of the injection provider's hand(s).

Finally, with reference to FIGS. 1, 2, 5, and 12, a delivery mechanism attachment 28 comprises a fixture configured to receive a delivery mechanism 8 and/or orientation structure 6 and hold it in fixed mechanical communication with the control syringe 4, yet permitting fluid communication between the delivery mechanism 8 and control syringe 4.

Referring to FIGS. 1, 6, 9A-C, a precision steerable and angled medication delivery system 2 may comprise a semi-rigid channel orientation structure 500. A semi-rigid channel orientation structure 500 may comprise an orientation structure 6 that is fixable at a desired angle. For example, the semi-rigid channel orientation structure 500 may comprise an arcuate portion 42, an inner linear portion 44, and a distal linear portion 46. The inner linear portion 44 may extend outwardly in a longitudinal direction away from the control syringe 4 for an offset distance 40. The inner linear portion 44 may terminate at an arcuate portion 42 which comprises a bend radius 36. The arcuate portion 42 may comprise a variety of different arc lengths, for instance, to dispose a distal linear portion 46 at a bend angle 38 relative to the inner linear portion 44 and correspondingly, relative to the longitudinal axis of the control syringe 4. As such, the arcuate portion 42 extends outwardly from the inner linear portion 44 and has a bend radius 36 configured to dispose the distal linear portion 46 at a bend angle 38. The bend radius 36 may be sufficiently large to prevent pinching of the delivery mechanism 8 so that medication may flow through an internal passage of the delivery mechanism 8. The distal linear portion 46 extends outwardly from the arcuate portion 42 having a bend angle 38 measured relative to the inner linear portion 44.

In various embodiments, a bend angle 38 of between 60 and 120 degrees is adopted, while in further embodiments, a bend angle 38 of between 70 and 110 degrees, or of between 80 and 100 degrees, or of between 85 and 95 degrees or of any bend angle 38 as desired, may be implemented. In various embodiments, a bend angle 38 of 90 degrees (+/−3 degrees) is implemented. In further embodiments, a bend angle 38 of less than 90 degrees is desired, in order to maintain vector components in at least two different orthogonal directions. For instance, a bend angle 38 may be between 50 and 110 degrees, or 60 and 100 degrees, or 70 and 90 degrees. In further embodiments, a bend angle 38 of approximately 75 degrees (+/−3 degrees) is implemented, while in further embodiments, a bend angle 38 of 80 degrees (+/−3 degrees) is implemented. In various embodiments, a bend angle 38 may be between 30 and 150 degrees (+/−3 degrees), or 70 and 110 degrees (+/−3 degrees), or may be 90 degrees (+/−3 degrees).

Figure 10:
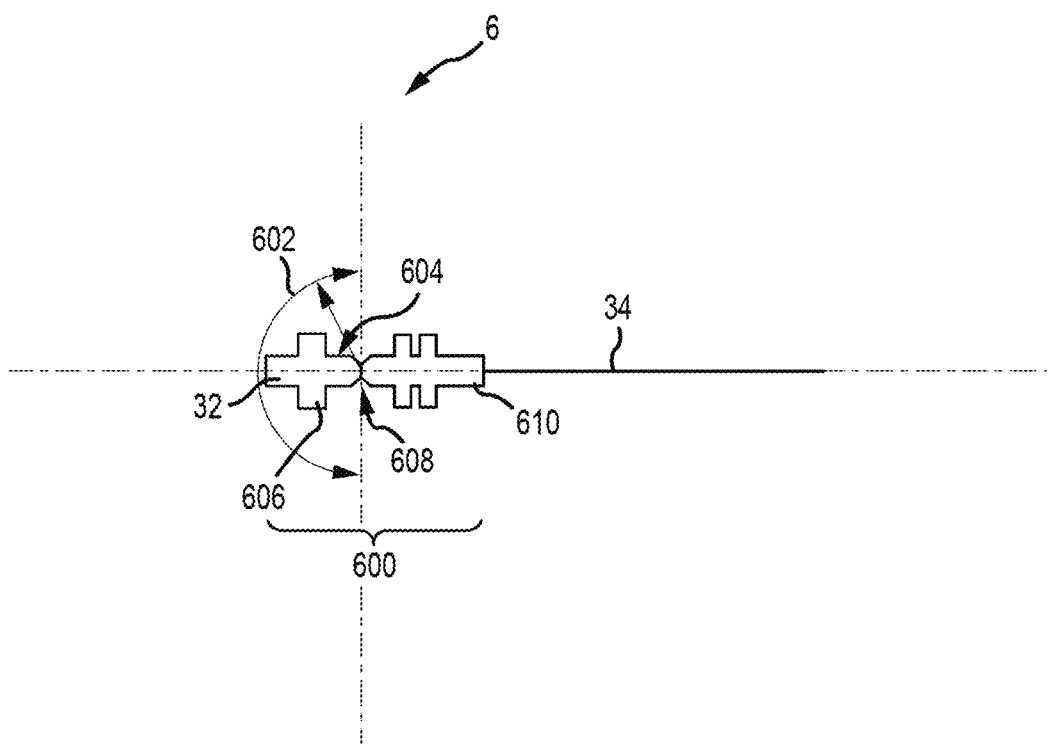
FIG. 10 depicts a variable bend connector orientation structure.

Referring to FIGS. 1, and 10, a precision steerable and angled medication delivery system 2 may comprise a variable bend connector orientation structure 600. A variable bend connector orientation structure 600 may comprise a control syringe attachable portion 606 and a delivery mechanism attachable portion 610 joined together by a fluid tight hinge 608. The control syringe attachable portion 606 may connect to the control syringe 4 at a delivery mechanism attachment 28 (FIGS. 1, 2) and may receive fluid from the control syringe 4. The fluid may be conducted through the fluid tight hinge 608 to the delivery mechanism attachable portion 610. The delivery mechanism attachable portion 610 may attach to a delivery mechanism 8 (FIGS. 1, 2) and may conduct fluid received via the fluid tight hinge 608 into the delivery mechanism 8 for delivery to a patient. For instance, a delivery mechanism 8, such as a needle 34, may be integrated with the variable bend connector orientation structure 600. In further instances, the delivery mechanism 8, such as a needle 34, may be attachable to the variable bend connector orientation structure 600. In various instances, the variable bend orientation structure 600 may be an aspect of the control syringe 4 such that the control syringe attachable portion 606 is permanently united with the control syringe 4. The variable bend orientation structure 600 may be a same piece of material as at least part of the control syringe 4. The variable bend orientation structure 600 may be a part of the control syringe 4. The needle 34 may be part of the variable bend orientation structure 600. The variable bend orientation structure 600 may be selectably connectable to both the control syringe 4 and the needle 34. The fluid tight hinge 608 may be articulable along an articulation path 602. In various embodiments, the articulation path 602 comprises an arc, though any other shape may be considered as desired. The fluid tight hinge 608 assumes an articulation angle 604 along the articulation path 602, whereby the delivery mechanism attachable portion 610 and the control syringe attachable portion 606 may be angled relative to one another, so that, correspondingly, a delivery mechanism 8 may be directionally controllable relative to the control syringe 4.

The control syringe attachable portion 606 is configured to connect to a delivery mechanism attachment 28 of a control syringe 4 and extend outwardly away from the control syringe 4, a fluid tight hinge 608 joins a delivery mechanism attachable portion 610 to the control syringe attachable portion 606, while a fluid tight hinge 608 translates the delivery mechanism attachable portion 610 along an arcuate articulation path 602. An articulation angle 604 may be selectably fixed between the delivery mechanism attachable portion 610 and the control syringe attachable portion 606. The fluid tight hinge 608 is selectably fixable along the arcuate articulation path 602, wherein the articulation angle 604 is unchangeable. In further embodiments, the articulation angle 604 is selectably changeable. The control syringe attachable portion 606 may be connected to a control syringe 4, and the delivery mechanism 8 may be a hollow needle 34.

Figure 11:
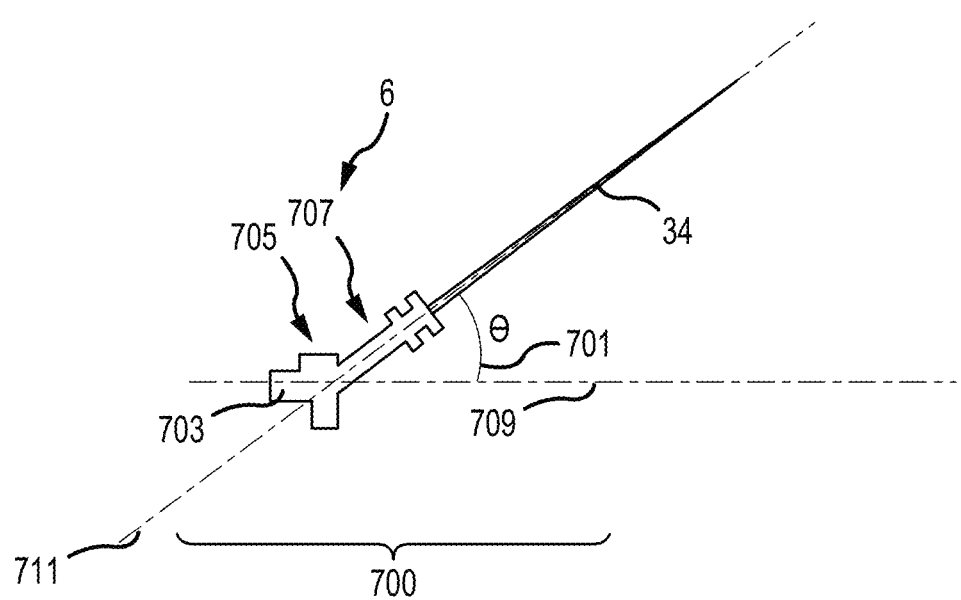
FIG. 11 depicts a fixed bend connector orientation structure.

Referring to FIGS. 1 and 11, the orientation structure 6 may comprise a fixed bend connector orientation structure 700. A fixed bend connector orientation structure 700 may comprise a bent connector body 703 with a main chamber 705 and a secondary chamber 707. A bent connector body 703 may comprise an integrally formed structure connectable to both the delivery mechanism attachment 28 of the control syringe 4 (FIGS. 1-2) and to the delivery mechanism 8. In various embodiments a fixed bend connector orientation structure 700 is connected to the control syringe 4 and connectable to the delivery mechanism 8. In various further embodiments, a fixed bend connector orientation structure 700 is connectable to the control syringe 4 and connected to the delivery mechanism 8.

A delivery mechanism 8, such as a needle 34, may be integrated with the fixed bend connector orientation structure 700. In further instances, the delivery mechanism 8, such as a needle 34, may be attachable to the fixed bend connector orientation structure 700. The bent connector body 703 may have a fixed bend angle 701. The fixed bend angle 701 may comprise a relative angle between longitudinal axes (first longitudinal axis 709, second longitudinal axis 711) of each distal end of the bent connector body 703, thus the fixed bend angle 701 may comprise a relative angle between the control syringe 4 to the delivery mechanism 8. Consequently, a bent connector body 703 may be connected to a delivery mechanism attachment 28 of a control syringe 4 and may establish a fixed bend angle 701 between a longitudinal axis (second longitudinal axis 711) of a distal end of the bent connector body 703 and a syringe longitudinal axis (first longitudinal axis 709) of the control syringe 4.

In various embodiments, a fixed bend angle 701 of between 60 and 120 degrees is adopted, while in further embodiments, a fixed bend angle 701 of between 70 and 110 degrees, or of between 80 and 100 degrees, or of between 85 and 95 degrees or of any fixed bend angle 701 as desired, may be implemented. In various embodiments, a fixed angle 701 may be between 30 and 150 degrees (+/−3 degrees), or 70 and 110 degrees (+/−3 degrees), or may be 90 degrees (+/−3 degrees). In further embodiments, a fixed bend angle 701 of less than 90 degrees is desired, in order to maintain vector components in at least two different orthogonal directions. For instance, a fixed bend angle 701 may be between 50 and 110 degrees, or 60 and 100 degrees, or 70 and 90 degrees. In further embodiments, a fixed bend angle 701 of approximately 75 degrees (+/−3 degrees) is implemented, while in further embodiments, a fixed bend angle 701 of 80 degrees (+/−3 degrees) is implemented.

Figure 12:
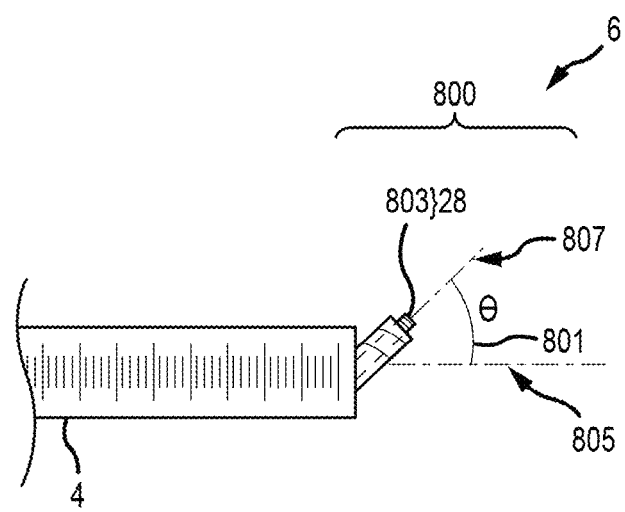
FIG. 12 depicts an integral syringe channel orientation structure.

Referring to FIGS. 1 and 12, the orientation structure 6 may comprise an integral syringe channel orientation structure 800. An integral syringe channel orientation structure 800 may comprise an angled delivery mechanism attachment 803 disposed at the distal end of a control syringe 4. In other embodiments, such as having an arcuate or angled control syringe 4, the angling of the angled delivery mechanism attachment 803 may arise from the arcuate or angled nature of the control syringe 4. With such an arcuate or angled control syringe 4, instead of having a longitudinal axis, such control syringe may be thought of as having a curved or arcuate central axis. The angled delivery mechanism attachment 830 may comprise a species of delivery mechanism attachment 28 (FIG. 1-2) having an angle relative to the syringe central longitudinal axis 805. For instance, a delivery mechanism central longitudinal axis 807 of the angled delivery mechanism attachment 803 may form a syringe bend angle 801 relative to a syringe central longitudinal axis 805.

Thus, an integral syringe channel orientation structure 800 extends from a distal end of the control syringe 4. The integral syringe channel orientation structure 800 is connectable to a delivery mechanism 8. The delivery mechanism 8 may comprise a needle 34. The integral syringe channel orientation structure 800 may comprise an angled delivery mechanism attachment 803 configured to orient the needle 34 at a syringe bend angle 801 relative to a syringe longitudinal axis of the control syringe 4.

In various embodiments, a syringe bend angle 801 of between 60 and 120 degrees is adopted, while in further embodiments, a syringe bend angle 801 of between 70 and 110 degrees, or of between 80 and 100 degrees, or of between 85 and 95 degrees or of any syringe bend angle 801 as desired, may be implemented. In various embodiments, a syringe bend angle 801 may be between 30 and 150 degrees (+/−3 degrees), or 70 and 110 degrees (+/−3 degrees), or may be 90 degrees (+/−3 degrees). In further embodiments, a syringe bend angle 801 of less than 90 degrees is desired, in order to maintain vector components in at least two different orthogonal directions. For instance, a syringe bend angle 801 may be between 50 and 110 degrees, or 60 and 100 degrees, or 70 and 90 degrees. In further embodiments, a syringe bend angle 801 of approximately 75 degrees (+/−3 degrees) is implemented, while in further embodiments, a syringe bend angle 801 of 80 degrees (+/−3 degrees) is implemented.

Figure 13A:
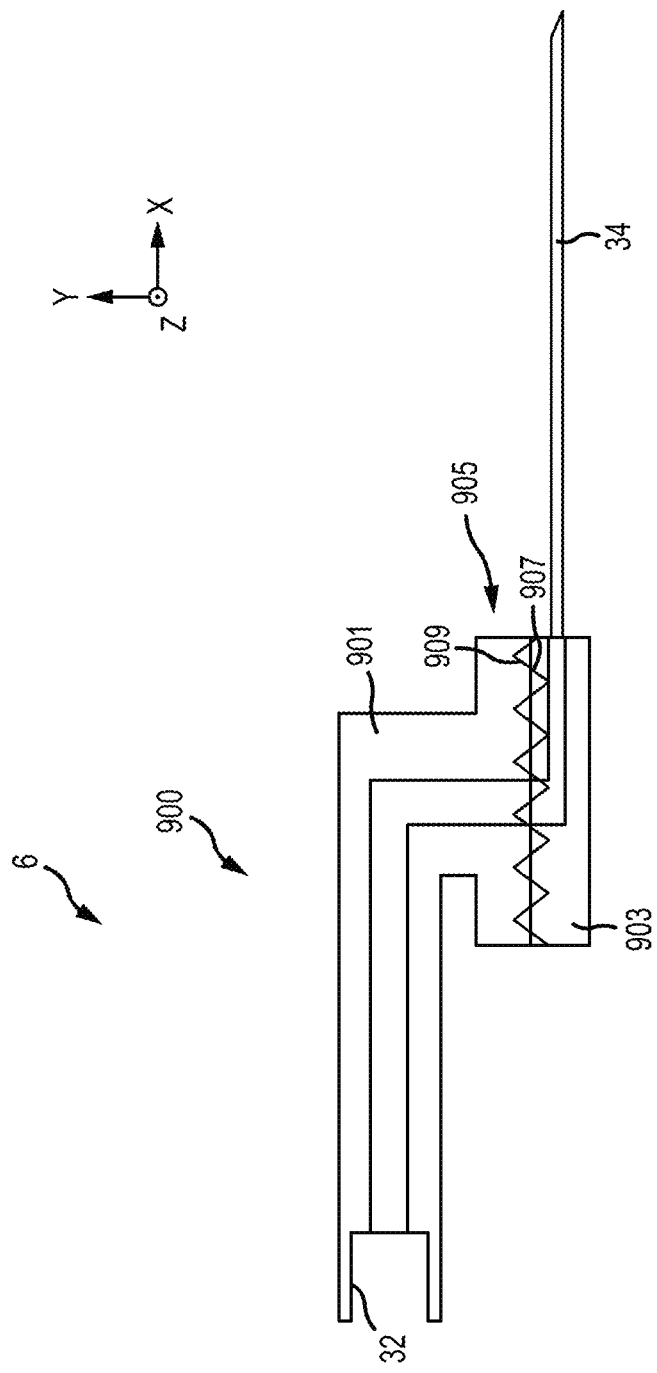
FIGS. 13A-B depict a rotatable connector orientation structure.
Figure 13B:
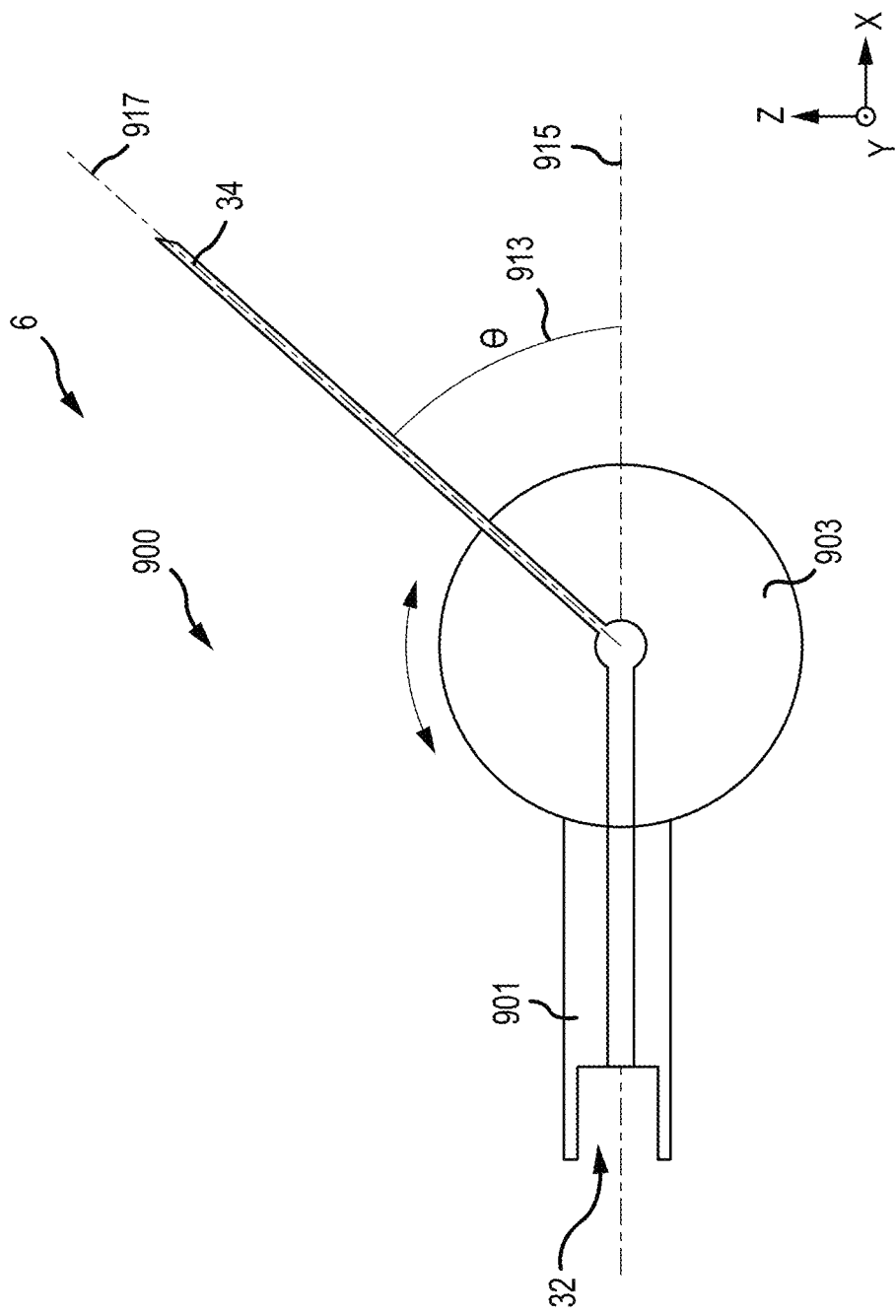

Referring to FIGS. 1 and 13A-B, the orientation structure 6 may comprise a rotatable connector orientation structure 900. A rotatable connector orientation structure 900 may comprise a main body 901 having a main body central longitudinal axis 915. The main body 901 may have a control syringe attachable portion 606 configured to connect to the control syringe 4 at the delivery mechanism attachment 28 (FIGS. 1, 2), and may extend outwardly away from the control syringe 4. The main body 901 may be slidably joined to a rotatable body 903. The rotatable body 903 may be connectable to a control syringe attachment 32 of a delivery mechanism 8. For instance, a delivery mechanism 8, such as a needle 34, may be integrated with the rotatable connector orientation structure 900. In further instances, the delivery mechanism 8, such as a needle 34, may be attachable to the rotatable connector orientation structure 900. A position setting interface 905 may be interstitially disposed between the rotatable body 903 and main body 901. More specifically, a position setting interface 905 comprises first surface 907 comprising a mesial face of the rotatable body 903 relative to the main body 901 and a second surface 909 comprising mesial face of the main body 901 relative to the rotatable body 903. The faces may be frictionally interlocked, for instance, each having conjugate serrations, so that the orientation of the rotatable body 903 relative to the main body 901 may be variable, yet also securely fixable. The rotatable body 903 may have a rotatable body orientation axis 917 extending from the center of the rotatable body 903 through a delivery mechanism 8 formed with or attachable thereto. For instance, the delivery mechanism 8 may be a needle 34 extending therefrom. The rotatable body orientation axis 917 and the main body central longitudinal axis 915 may form a rotation angle 913.

In various embodiments, a rotation angle 913 of between 60 and 120 degrees is adopted, while in further embodiments, a rotation angle 913 of between 70 and 110 degrees, or of between 80 and 100 degrees, or of between 85 and 95 degrees or of any rotation angle 913 as desired, may be implemented. In various embodiments, a rotation angle 913 may be between 30 and 150 degrees (+/−3 degrees), or 70 and 110 degrees (+/−3 degrees), or may be 90 degrees (+/−3 degrees). In further embodiments, a rotation angle 913 of less than 90 degrees is desired, in order to maintain vector components in at least two different orthogonal directions. For instance, a rotation angle 913 may be between 50 and 110 degrees, or 60 and 100 degrees, or 70 and 90 degrees. In further embodiments, a rotation angle 913 of approximately 75 degrees (+/−3 degrees) is implemented, while in further embodiments, a syringe bend angle 801 of 80 degrees (+/−3 degrees) is implemented.

Figure 3:
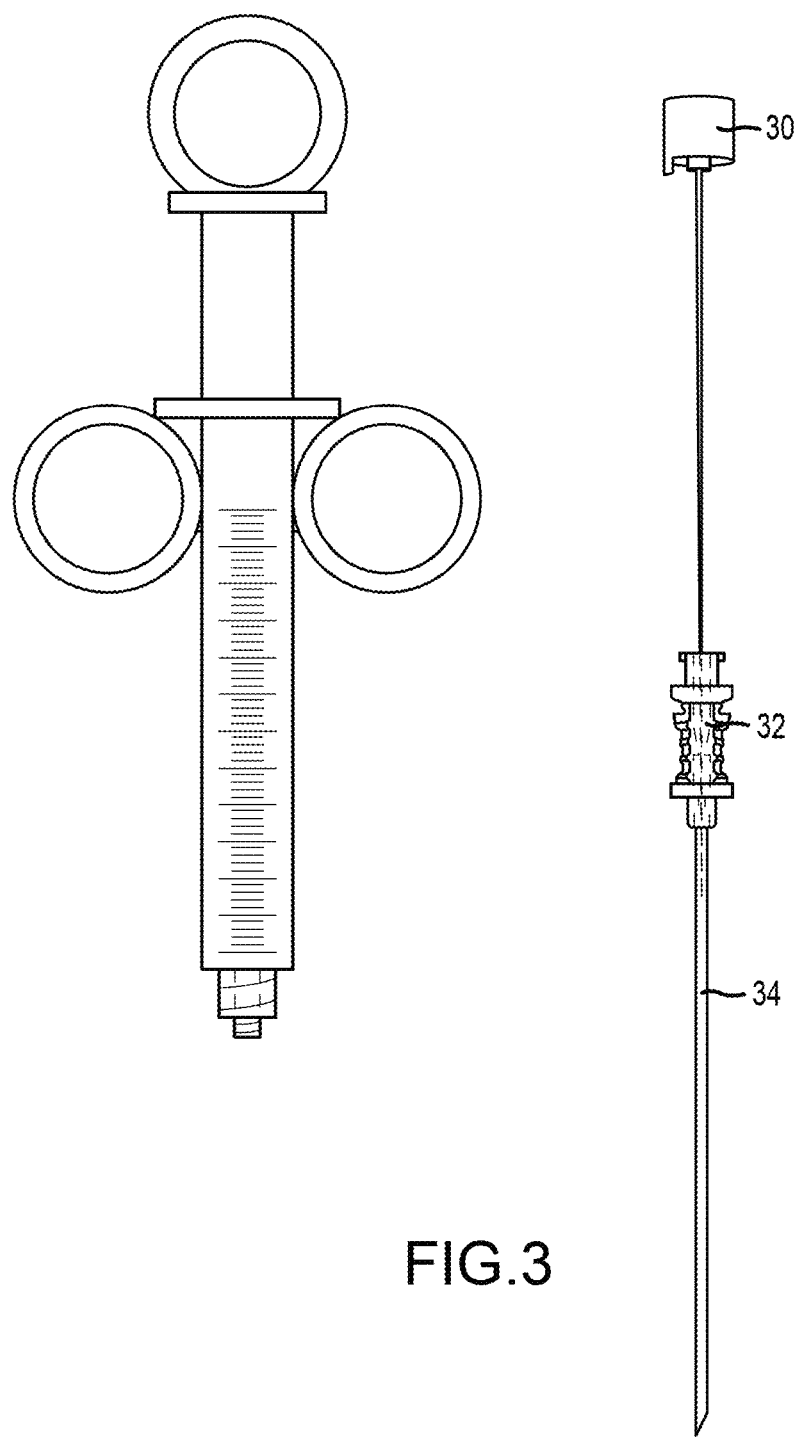
Figure 4:
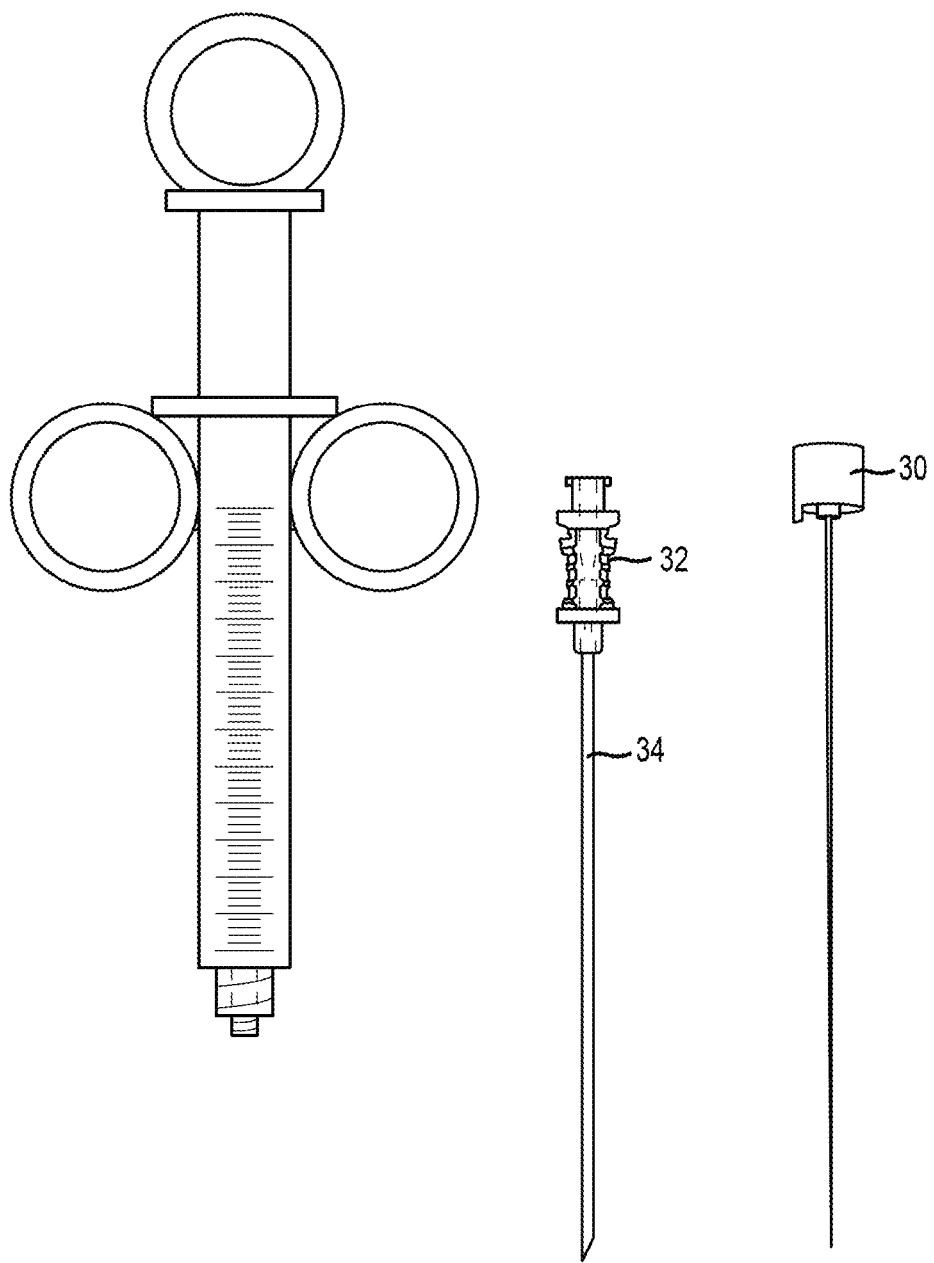
Figure 5:
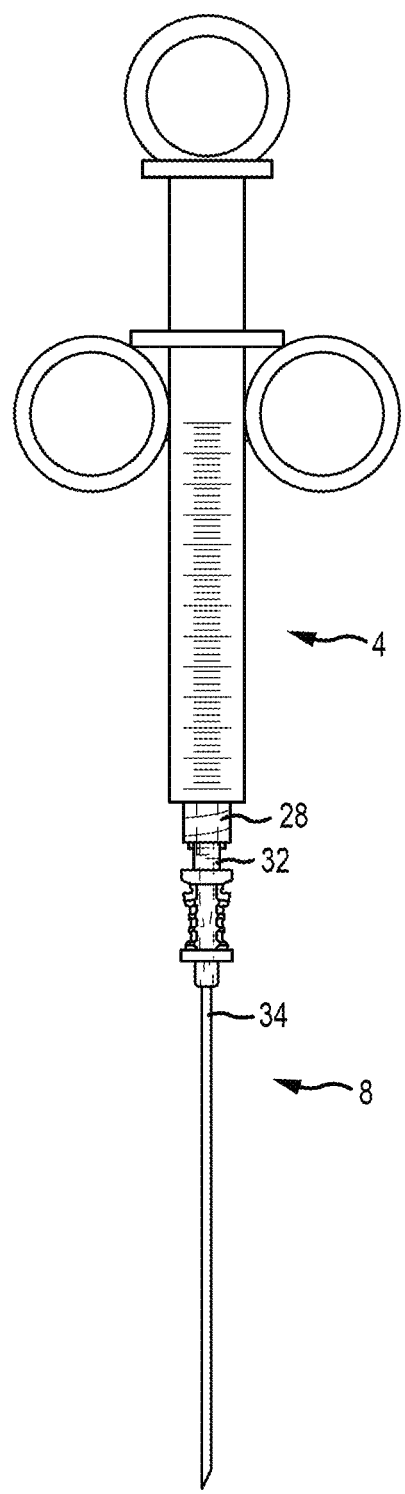
Figure 17:
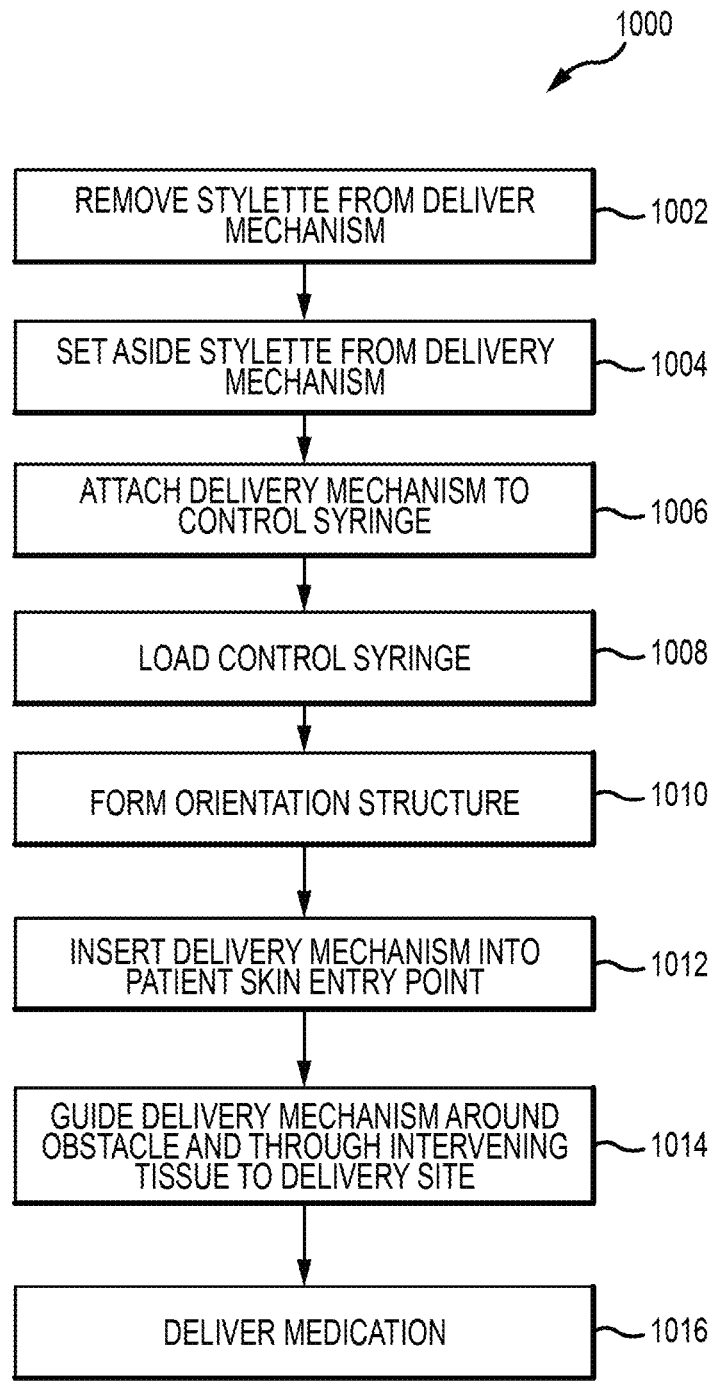
FIG. 17 depicts a method of directionally controlled medication delivery.

Having discussed various structural aspects of a precision steerable and angled medication delivery system 2, reference is directed to FIGS. 1-16, with additional reference to FIG. 17. A method of directionally controlled medication delivery 1000 may include various steps. For instance, an injection provider may remove a stylette 30 from a delivery mechanism 8 (step 1002) as shown in FIG. 3. The stylette 30 may be set aside from the delivery mechanism 8 (step 1004) as shown in FIG. 4. The delivery mechanism 8 is connected to the control syringe 4 (step 1006) as shown in FIG. 5 and the control syringe 4 is loaded with medication (step 1008). Finally, an orientation structure 6 is formed (step 1010).

Figure 6:
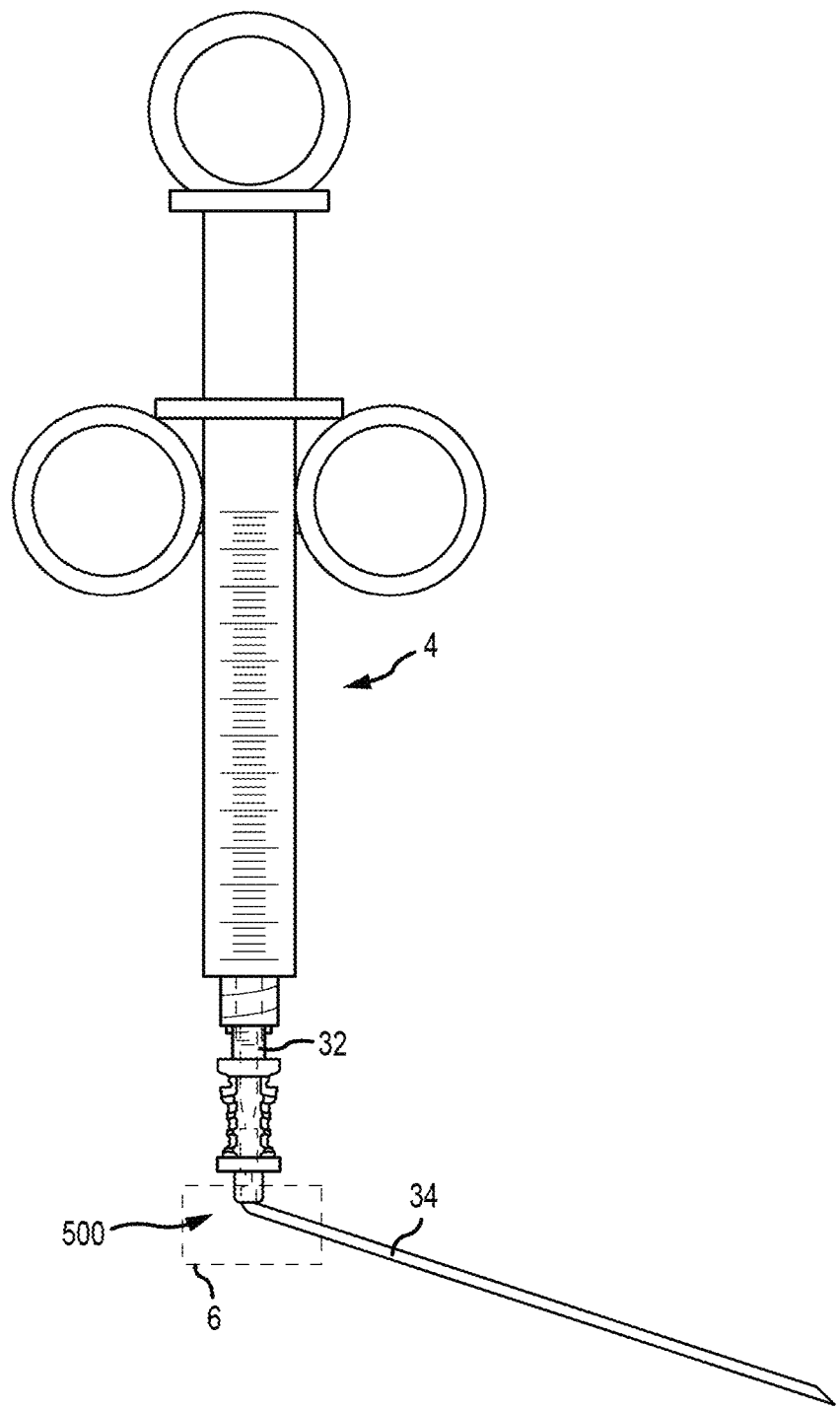
Figure 7:
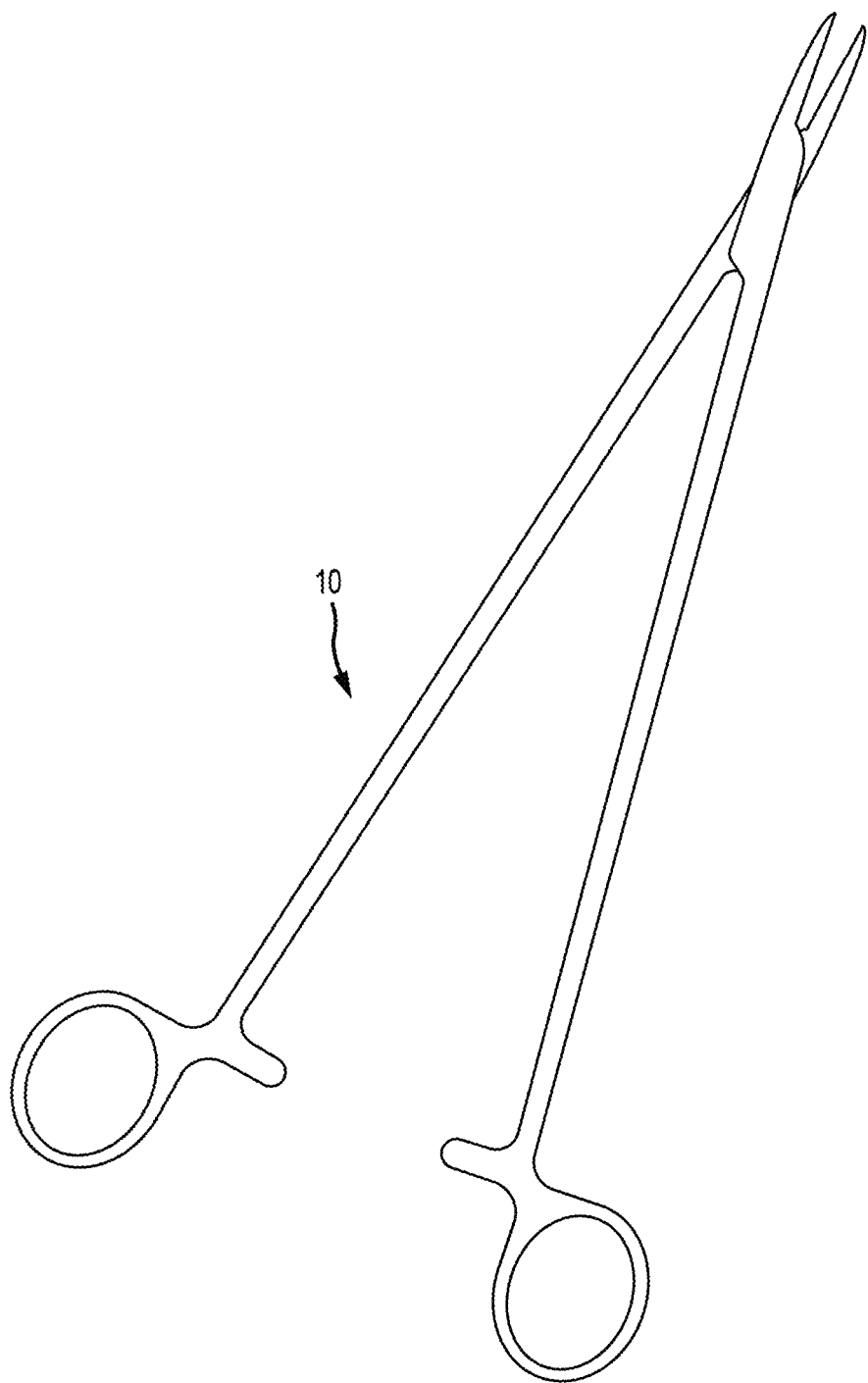
FIG. 7 depicts a stabilization structure for use in association with a precision steerable and angled medication delivery system.
Figure 8:
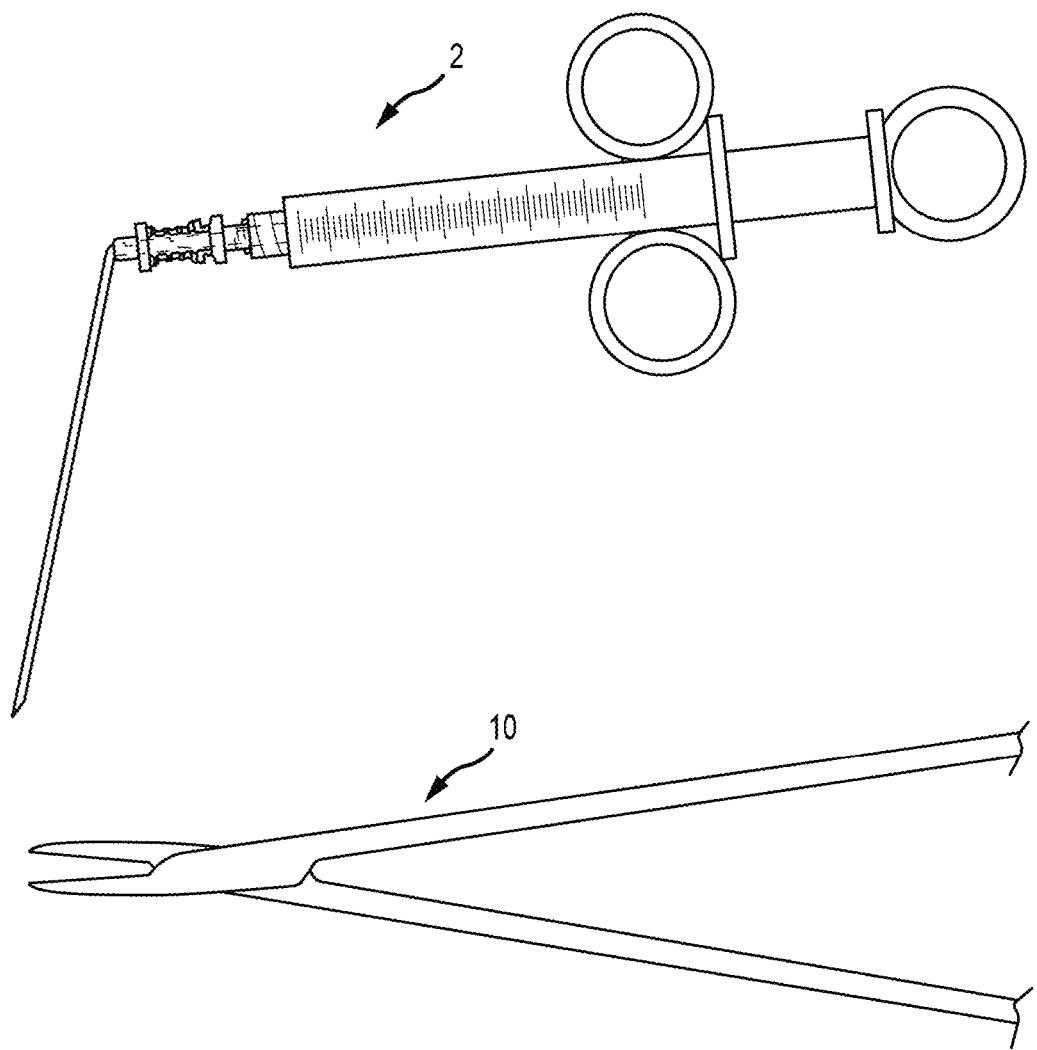
FIG. 8 depicts a stabilization structure and a precision steerable and angled medication delivery system together.
Figure 9A:
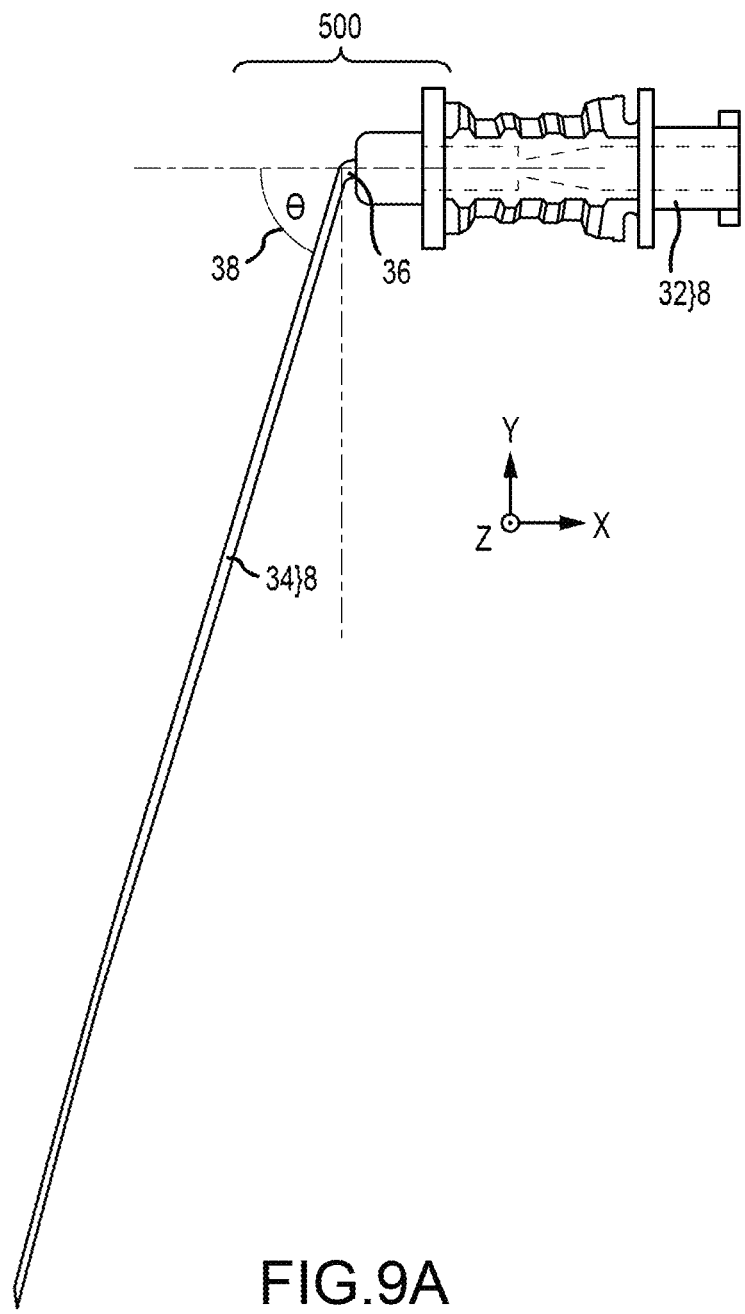
FIGS. 9A-C depict different views of an example semi-rigid channel orientation structure of a precision steerable and angled medication delivery system.
Figure 9B:
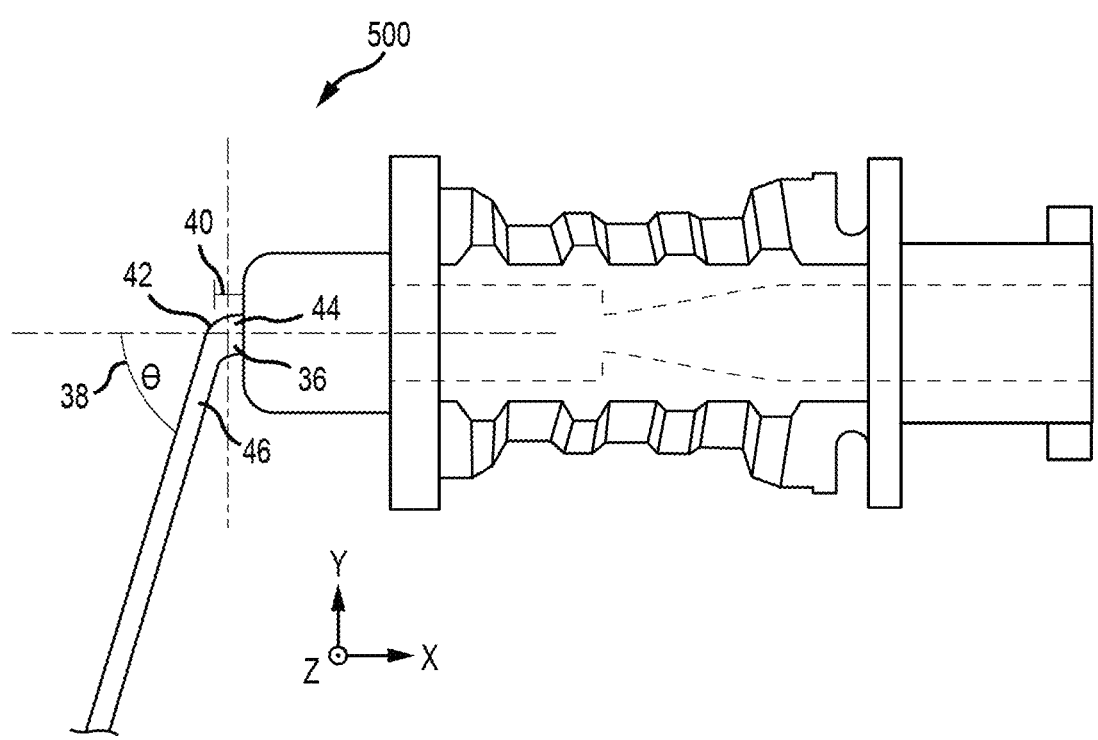
Figure 9C:
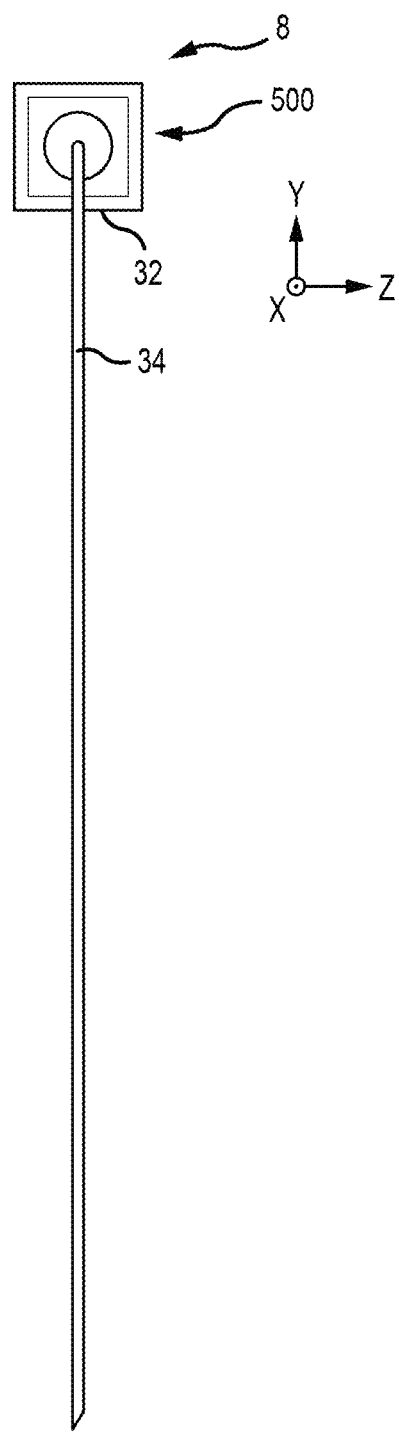

FIGS. 1 and 6 show an orientation structure 6 comprising a semi-rigid channel orientation structure 500 having been formed by bending a needle 34 of a delivery mechanism 8 to assume a bend angle 38 (FIG. 9A-C). In further embodiments, such as with reference to FIG. 10, forming an orientation structure 6 (step 1010) may involve adjusting a fluid tight hinge 608 of a variable bend connector orientation structure 600 to assume an articulation angle 604 along an articulation path 602. In further embodiments, with reference to FIG. 11, forming an orientation structure 6 (step 1010) simply involves attaching a fixed bend connector orientation structure 700 to a control syringe 4, since the bent connector body 703 has an fixed bend angle 701. In still further embodiments, with reference to FIG. 12, forming an orientation structure 6 (step 1010) simply involves attaching a delivery mechanism 8 directly to a control syringe 4 because the control syringe 4 includes an integral syringe channel orientation structure 800 with a syringe bend angle 801. Finally, and with reference to FIG. 13A-B, forming an orientation structure 6 (step 1010) may include choosing a rotation angle 913 of a rotatable connector orientation structure 900.

Subsequently, with reference to FIGS. 1, 2, 14-17, 19A-C, 20A-D, 21A-B, 22A-B, 23A-C, 24A-B, and 25A-C, the delivery mechanism 8 is inserted into the patient's skin 14 at an entry point 22 (step 1012). The insertion may be guided and encouraged by a stabilization structure 10, as is simulated in FIGS. 14-15. The delivery mechanism 8 is guided around obstacles 20 and through intervening tissue 18 to a delivery site 16 (FIG. 1) (step 1014). In various embodiments, positive pressure is maintained on the bidirectional control plunger 24 of the control syringe 4 during insertion, in order to prevent clogging of the needle 34. Finally, medication is delivered by depressing of the bidirectional control plunger 24 of the control syringe 4 (step 1016).

Figure 14:
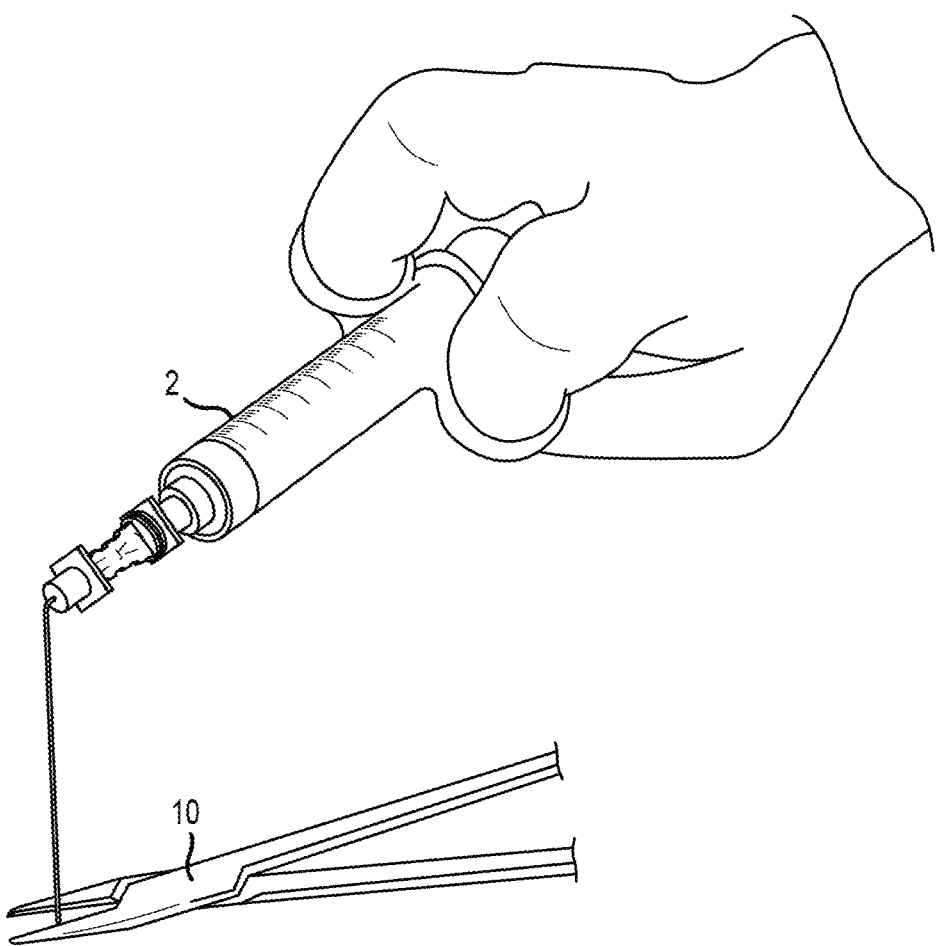
FIG. 14 depicts an example embodiment of a precision steerable and angled medication delivery system in connection with a stabilization structure.
Figure 15:
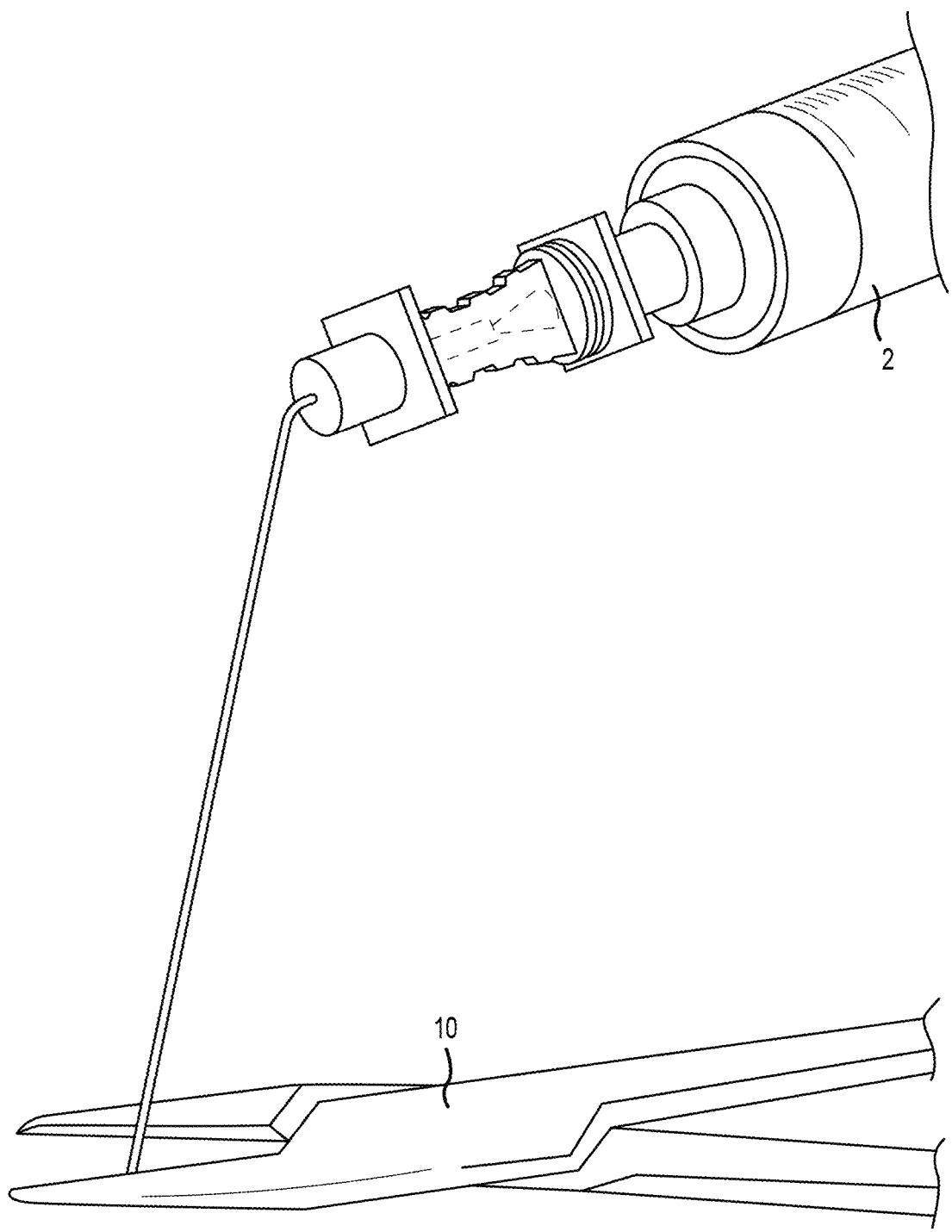
FIG. 15 depicts a close up view of a precision steerable and angled medication delivery system in connection with a stabilization structure.
Figure 16:
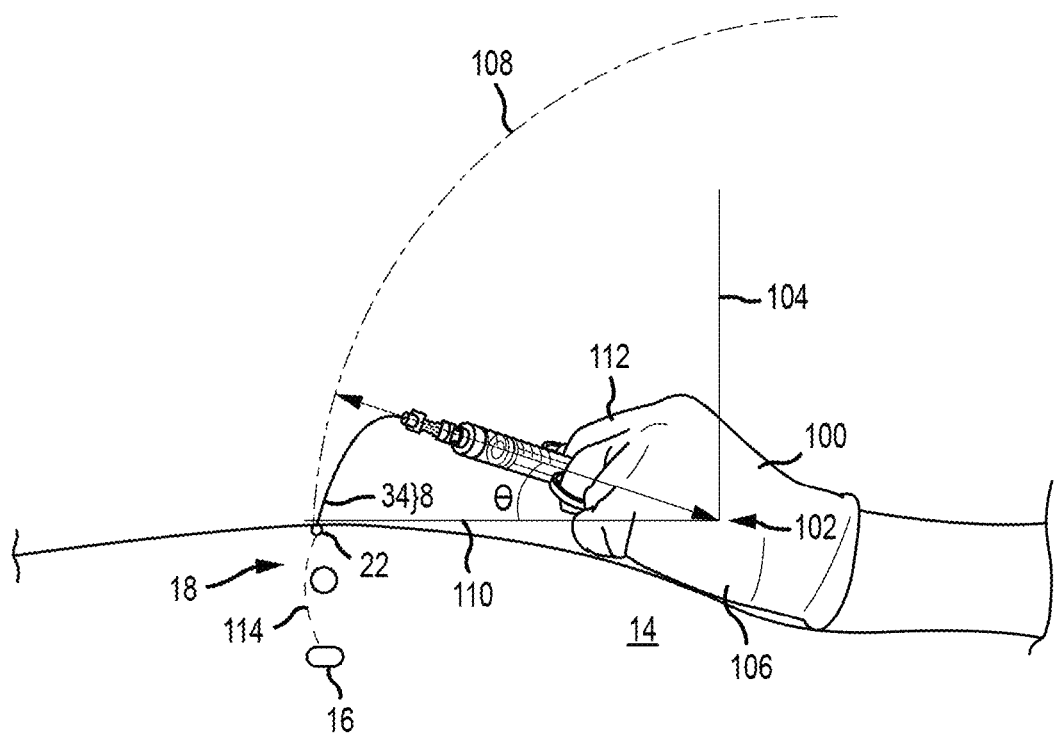
FIG. 16 depicts a directionally controlled medication delivery scenario.

Also, while the simulation of FIG. 14 depicts one particular embodiment of delivery mechanism 8 and control syringe 4, any combination of embodiments of delivery mechanisms 8 and control syringes 4 may be implemented. For instance, a control syringe 4 with an integral syringe channel orientation structure 800 (FIG. 12) may be implemented. Also, a control syringe 4 with a fixed bend connector orientation structure 700 (FIG. 11) may be implemented. Moreover and as shown in FIG. 14, a control syringe 4 and orientation structure may be oriented so that markings indicating a medication dose may be oriented away from a delivery mechanism 8 and opposite the delivery mechanism 8, whereby an injection provider may monitor the volume of the injection during delivery.

Figure 18:
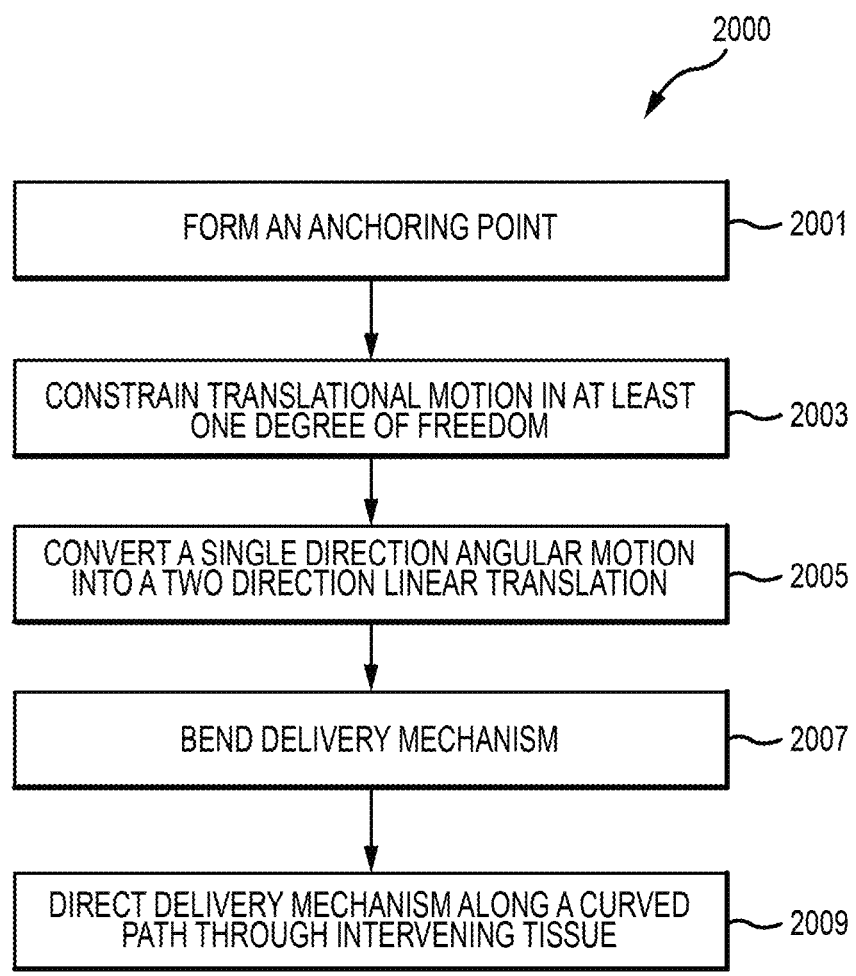
FIG. 18 depicts a method of delivery mechanism guidance.
Figure 19A:
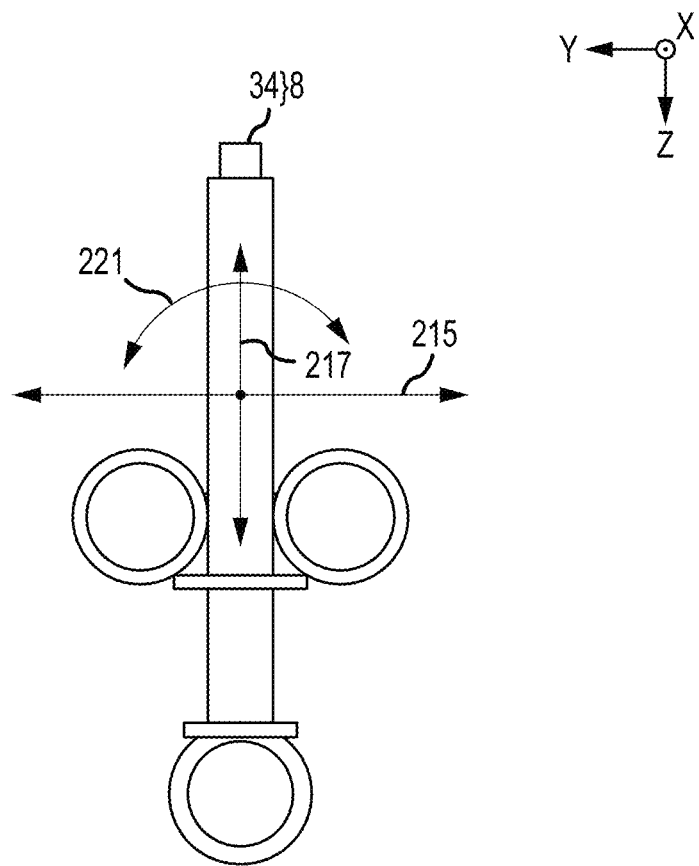
FIGS. 19A-D depict various degrees of freedom wherein a precision steerable and angled medication delivery system may be operable.
Figure 19B:
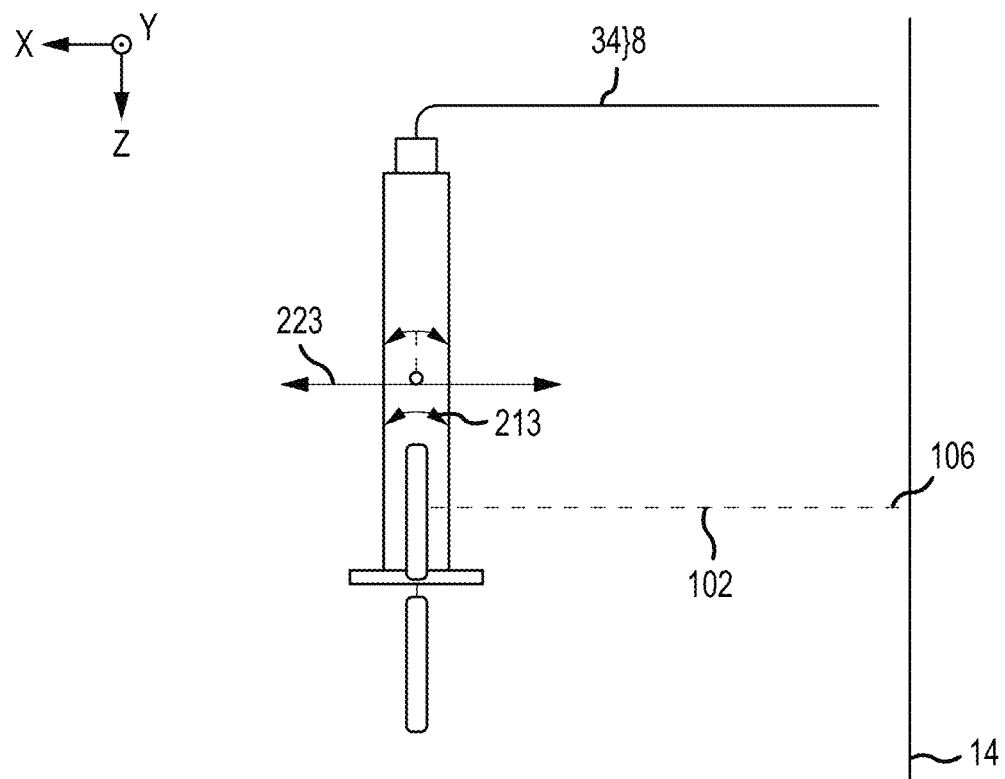
Figure 19C:
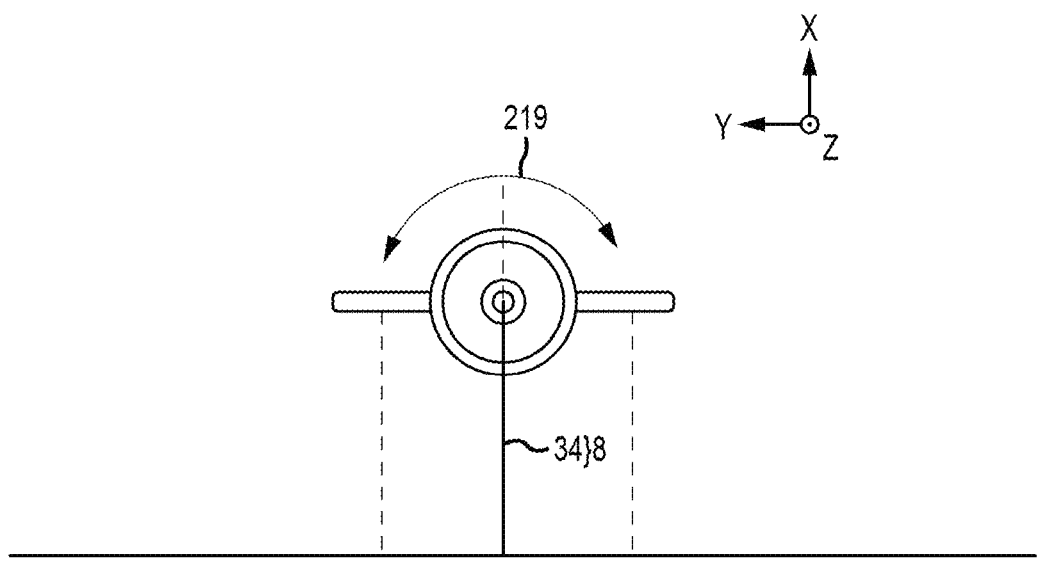
Figure 19D:
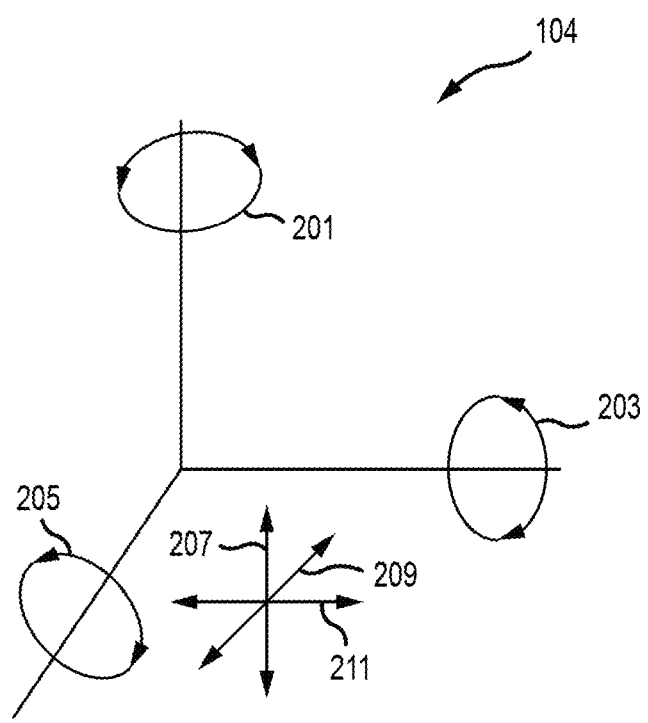
Figure 20A:
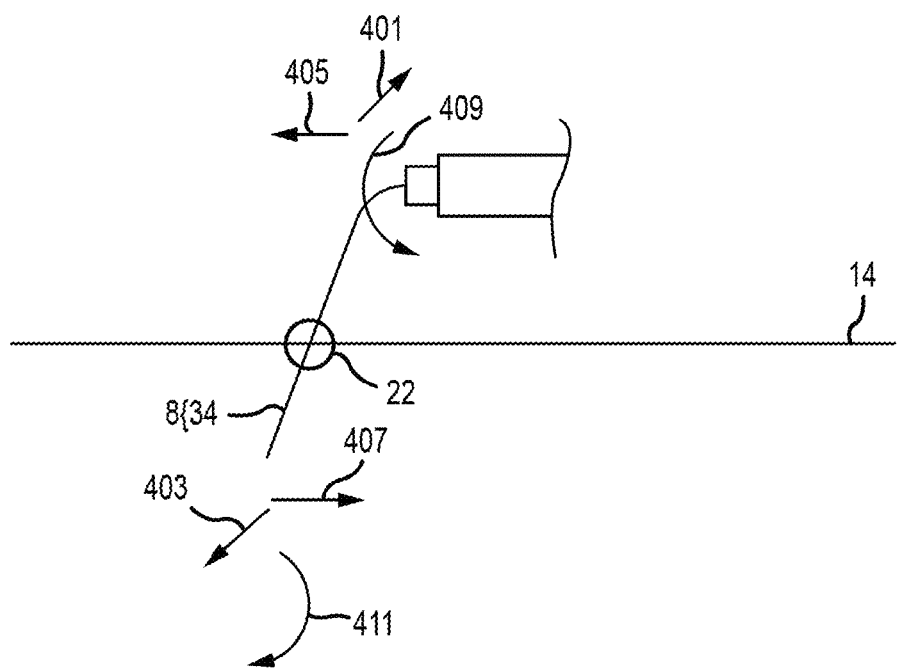
FIG. 20A depicts further aspects of a directionally controlled medication delivery scenario of FIG. 16.
Figure 20B:
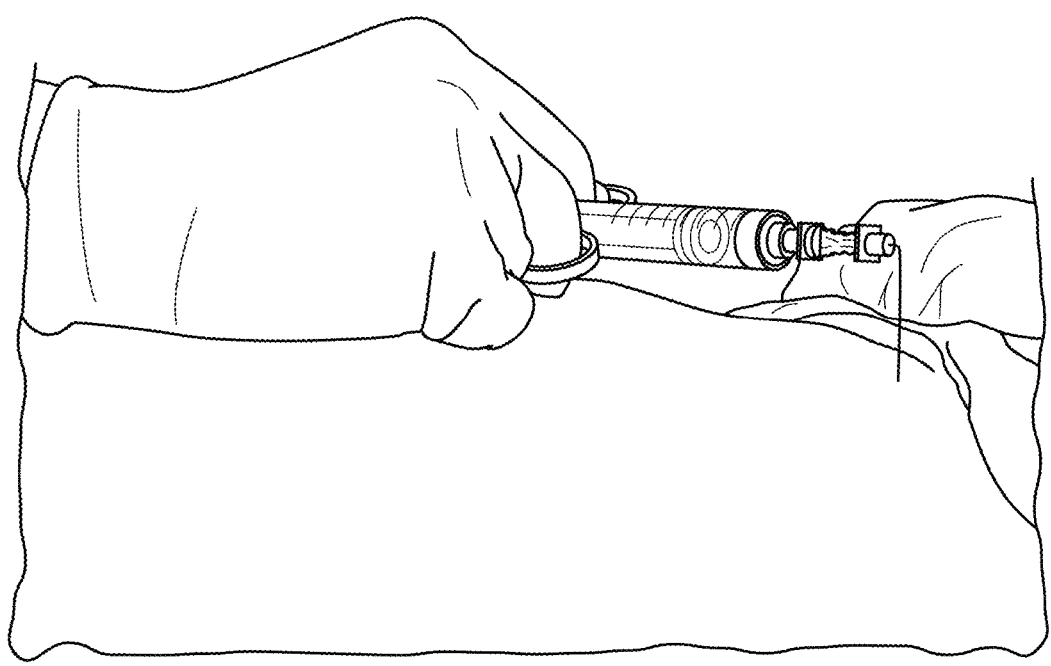
FIGS. 20B-D are images depicting aspects of a directionally controlled medication delivery scenario of FIG. 16 and FIG. 20A.
Figure 20C:
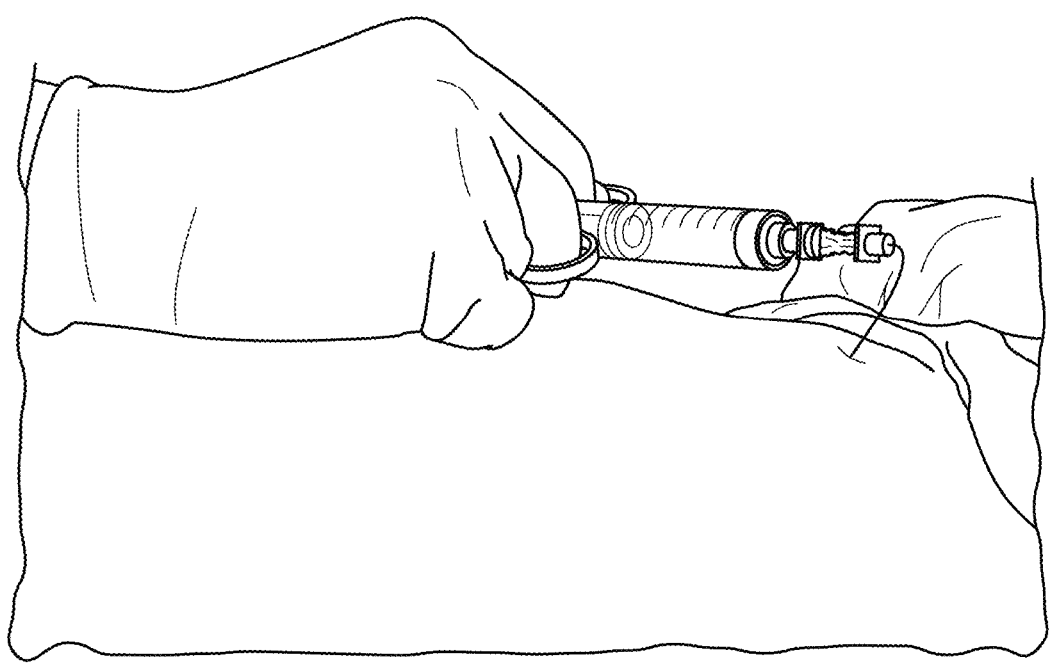
Figure 20D:
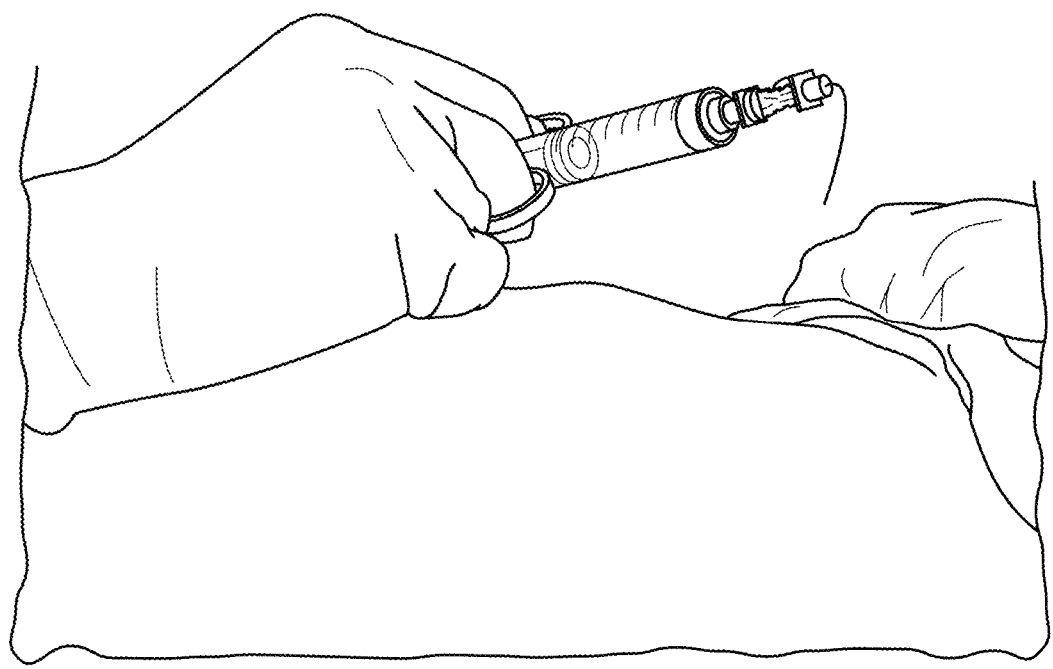

Turning now with additional reference to FIG. 18, steps 1012 and 1014 are discussed with more particularity. In various embodiments, particular methods are implemented whereby the insertion of the delivery method into the patient's skin 14 and/or the guidance of the delivery mechanism 8 to the delivery site 16 are effectuated. For instance, with particular emphasis on FIGS. 16, 19A-D, 20A-D, 21A-B, 22A-B, 23A-C, 24A-B, and 25A-C, a method of delivery mechanism guidance 2000 is disclosed. In various embodiments, an injection provider may form an anchoring pivot (step 2001). For example, the injection provider may rest his or her hand 100 against a surface, for instance, a patient's skin 14. By resting a hand, a pivot 102 is formed, for instance, an articulating joint such as a wrist joint is stabilized. In this manner, translational motion in at least one degree of freedom 104 is constrained (step 2003). Having constrained translational motion by anchoring the wrist at a fixed point 106, the angular motion 108 of the hand may be more readily controlled. The injection provider may grip a control syringe 4 of a precision steerable and angled medication delivery system 2. Because the delivery mechanism 8 of the precision steerable and angled medication delivery system 2 is angled by an orientation structure 6 relative to the control syringe 4, an arcuate motion pivoting in a single angular direction 108 causes the delivery mechanism 8 to pass through a path that can be decomposed into multiple orthogonal vector components 104, 110. Thus the precision steerable and angled medication delivery system 2 convert a single direction angular motion 108 of the control syringe 4 into a two direction linear translation 104, 110 of the delivery mechanism 8 (step 2005). As a consequence, the delivery mechanism 8 is readily steerable in at least two orthogonal degrees of freedom by a single arcuate motion. Furthermore, delivery mechanism 8 may be linearly translated under fine control by the relative motion of the user's fingers 112 yet while the wrist is anchored. Even furthermore, the injection provider may bend the delivery mechanism 8 to further steer it (step 2007). For instance the injection provider may use an entry point 22 of a patient skin to bend the delivery mechanism 8. As the delivery mechanism 8 penetrates a patient skin at an entry point 22, the entry point 22 affords a fulcrum to lever the delivery mechanism 8 against, impelling it to bend. By impelling the delivery mechanism 8 to bend, the delivery mechanism 8 may adopt a curved path 114 through the intervening tissue 18 of the patient (step 2009). As such, a first arcuate motion 108 may be translated into two linear motions 104, 110, which is then translated into a second arcuate motion 114. Three principles combine, specifically, anchoring of the wrist, a bend of the delivery mechanism 8, and levering the delivery mechanism 8 against the skin proximate to the entry point 22, in order to provide both accurate and flexible steerage of the delivery mechanism 8 while inside the body of the patient. The delivery mechanism 8 may pass around embedded obstacles 20 within the patient's body to a delivery site 16.

Figure 25A:
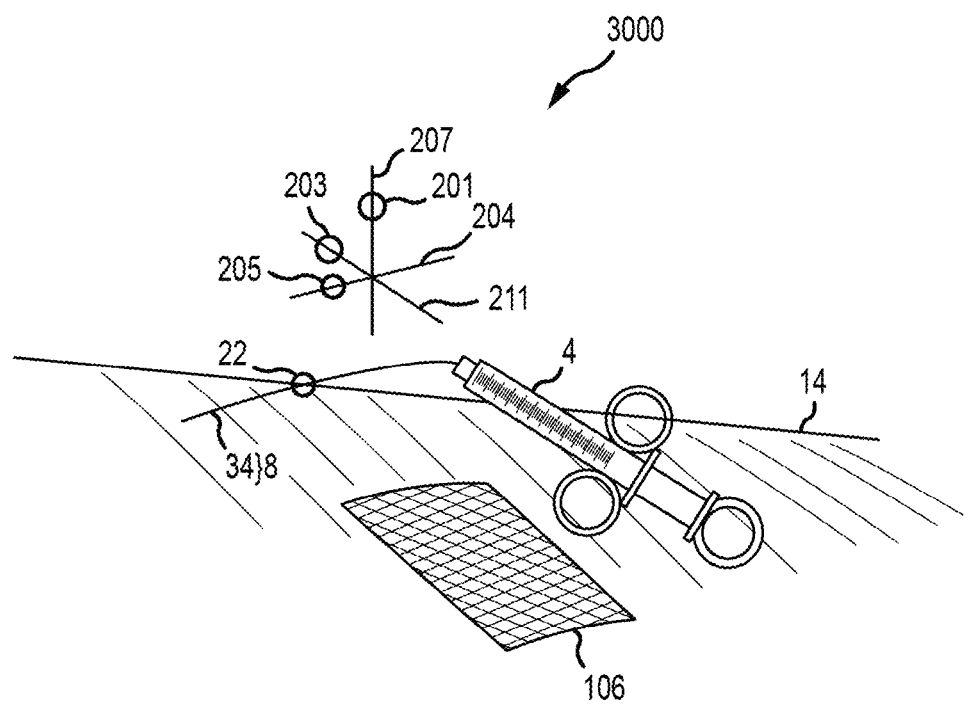
FIGS. 25A-C depict a shallow penetration directionally controlled medication delivery scenario.
Figure 25B:
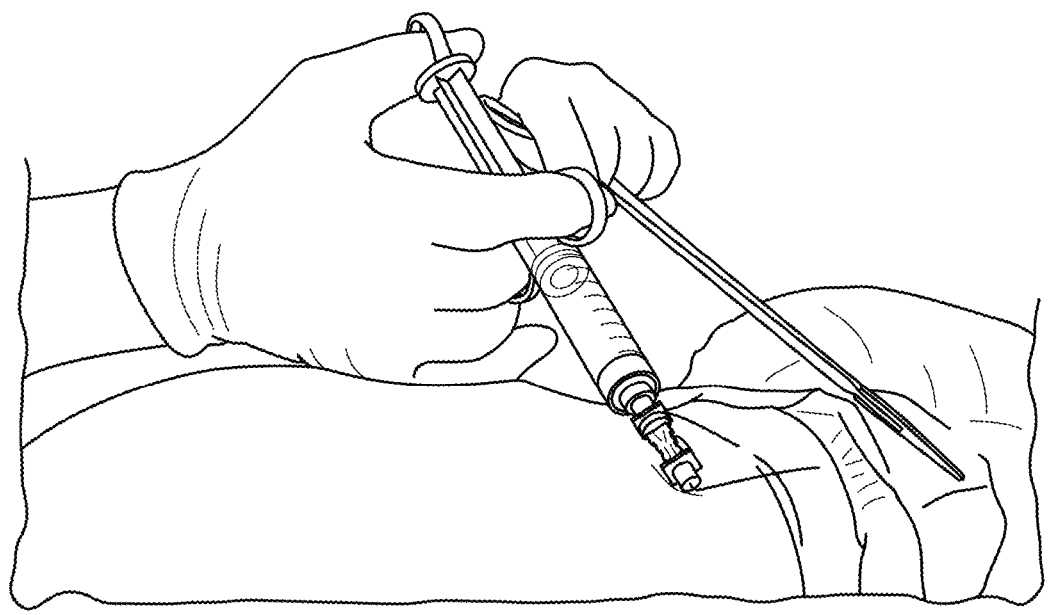
Figure 25C:
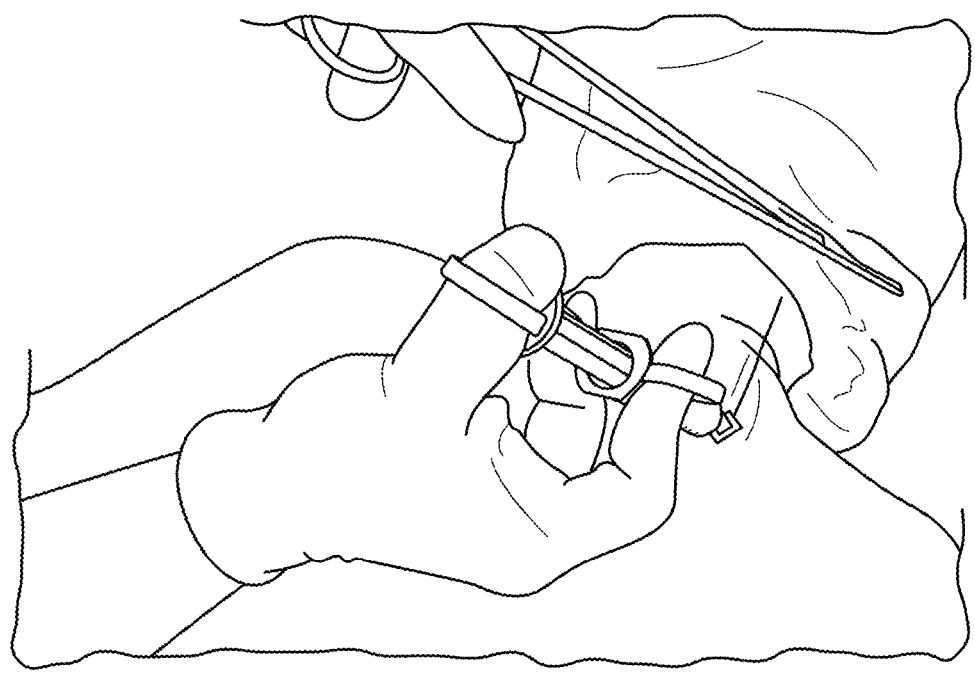

Continuing the discussion of a method of delivery mechanism guidance 2000, but with momentary emphasis on FIGS. 25A-C, the method 2000 may effectuate a shallow penetration directionally controlled medication delivery scenario 3000. For instance, by inserting the delivery mechanism 8 such as a needle 34 into the patient's skin 14 at an entry point 22 and positioning the control syringe 4 parallel to the surface of the patient's skin 13 the needle 34 may be guided along a shallow path near the surface of the skin 13. In this instance, the enhanced precision of the systems and methods taught herein facilitates close control of the delivery mechanism along the plane of the skin in addition to inwardly through the skin.

Thus, an injection provider may rest a first hand holding the control syringe 4 on a patient's body, pivot the control syringe 4 toward the patient's body along an curved path 108 whereby a needle 34 of the delivery mechanism 8 penetrates a patient's skin 14, and lever a needle 34 of the delivery mechanism 8 against the patient skin in a first direction, whereby a tip of the needle 34 travels in a direction opposite of the first direction and through the intervening tissue 18 around the obstacle along a second curved path 114 and to the delivery site 16.

Typically, an injection provider will rest a first hand holding the control syringe 4 on a patient's body to stabilize the control syringe 4 by removing one or more degrees of freedom of movement. As used herein, "degree of freedom" means, as shown in FIGS. 19D and 25A-C, a path 201, 203, 205, 207, 209, 211, or 223. A degree of freedom may be translational, such as along axes 207, 209, 211, or 223 or may be rotational, such as along arcs 201, 203, or 205.

During steerage of the control syringe 4, the pivoting along a curved path 108 may include a yaw 221 (FIG. 19A), a pitch 213 (FIG. 19B), a longitudinal axial roll 219 (FIG. 19C) or a combination of yaw 221, pitch 213 and longitudinal axial roll 219, as a curved path 108 may transit the different orthogonal domains.

During steerage of the control syringe 4, translational movements may also be incorporated. For instance, translation along a lateral direction 215, a longitudinal direction 217, an elevation direction 223 or a combination of lateral 215, longitudinal 217 and elevation 223 directions, as a translational path may transit the different orthogonal axes. Thus, as discussed above regarding method of delivery mechanism guidance 2000, the angular motion 108 may be in a variety or directions and may also be combined with translational motion. For example, the anchoring point 102 that is formed per FIG. 16 may be slidably translated across the patient's skin 14 so that translational motion may be incorporated without compromising the stabilizing effect with respect to the angular motion 108.

The combination of angular motion and translational motion is further detailed in FIGS. 20A-D. The entry point 22 forms a fulcrum so that a control syringe 4 translating in a forward longitudinal direction 405 may impel the needle 34 of the delivery mechanism 8 in an opposite direction, such as aft longitudinal direction 407, or a control syringe 4 translating in a right lateral direction 401 may impel the needle 34 of the delivery mechanism 8 in an opposite direction such as a left lateral direction 403. Moreover, the angular motion 108 may operate similarly such that a control syringe 4 rolling in a counterclockwise angular direction 409 may impel the needle 34 of the delivery mechanism 8 in an opposite direction such as a clockwise angular direction 411.

At various instances, translational motion may be combined with angular motion to cause a bending and a compression of the portion of the needle 34 outside the skin so that a point of inflection is formed outside of the skin, and thus outwardly of the entry point 22 which forms a fulcrum. Consequently, angular motion and translational motion may form points of inflection in the needle 34 which operate to direct the path of the needle 34 separately from, or in addition to, the influence of the fulcrum of the entry point 22. For instance, a control syringe 4 may be rotated in a longitudinal axial roll 219 and translated toward the patient's body along an elevation direction 223 so that the needle 34 is bent forming a point of inflection approximately midway between the control syringe 4 and the entry point 22, whereby the tip of the needle 34 is impelled to orient along a curved path downwardly from the point of inflection, through the entry point 22 and into the patient's body in a curved path.

Figure 21A:
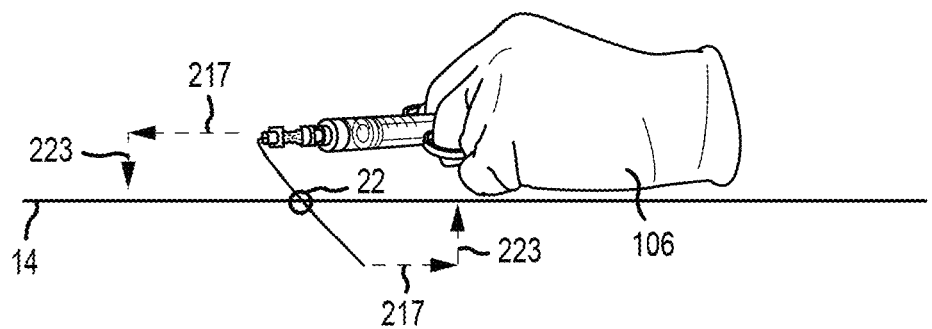
FIGS. 21A-B depict various movements of aspects of a precision steerable and angled medication delivery system including longitudinal translation.
Figure 21B:
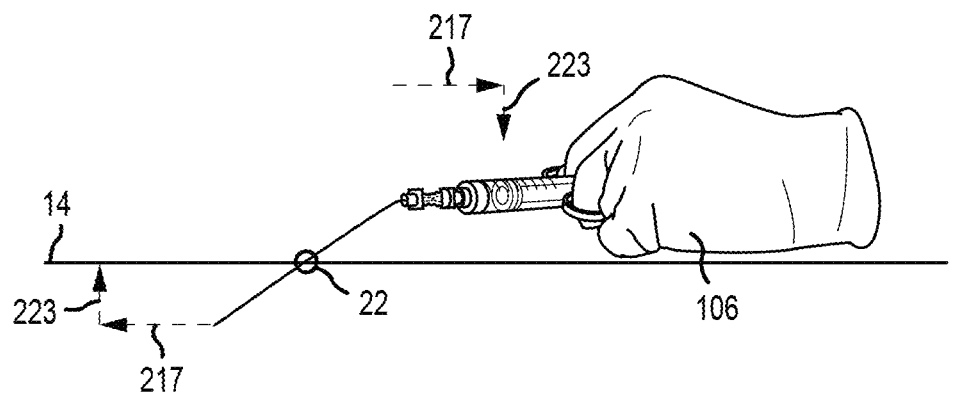

Various examples of such motions are provided. For example, with reference to FIG. 21A, a wrist is anchored at a fixed point 106 and slidably translates and/or the user manipulates the user's fingers to cause a control syringe 4 to positively translate in longitudinal direction 217 and an elevation direction 223 so that the needle 34 negatively translates in a longitudinal direction 217 and an elevation direction 223. With reference to FIG. 21B, a wrist is anchored at a fixed point 106 and slidably translates and/or the user manipulates the user's fingers to cause a control syringe 4 to negatively translate in longitudinal direction 217 and positively translate in an elevation direction 223 so that the needle 34 positively translates in a longitudinal direction 217 and negatively translates in an elevation direction 223.

Figures 22A, 22B:
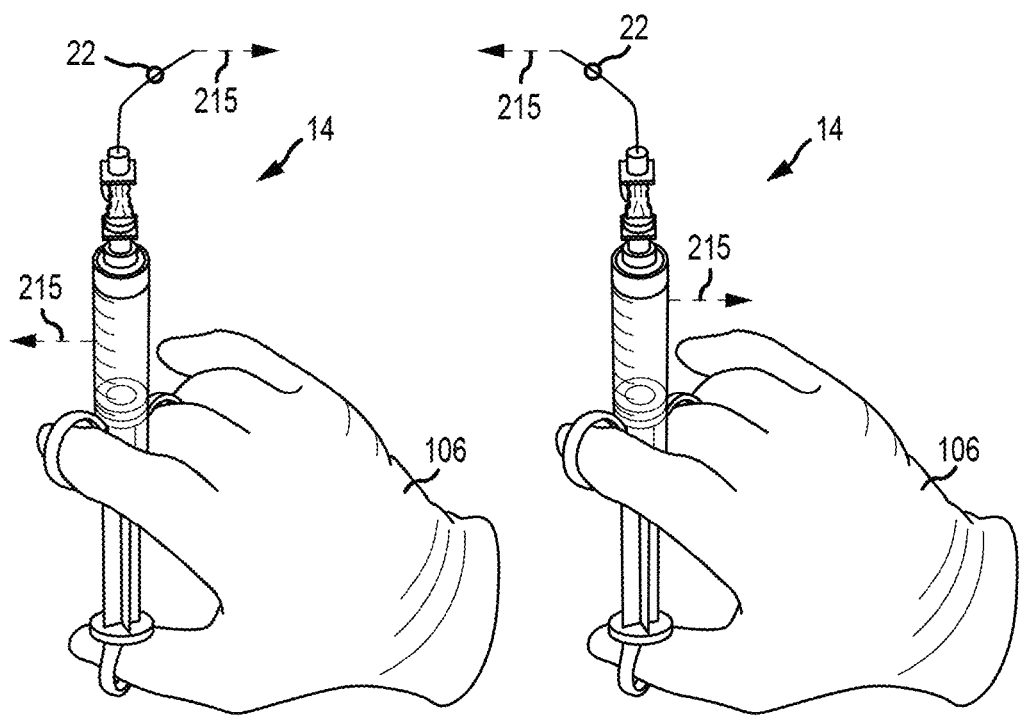
FIGS. 22A-B depict various movements of aspects of a precision steerable and angled medication delivery system including lateral translation.

With reference to FIG. 22A, a wrist is anchored at a fixed point 106 and slidably translates and/or the user manipulates the user's fingers to cause a control syringe 4 to positively translate in a lateral direction 215 so that the needle 34 negatively translates in a lateral direction 215, and similarly, with reference to FIG. 22B a wrist is anchored at a fixed point 106 and slidably translates and/or the user manipulates the user's fingers to cause a control syringe 4 to negatively translate in a lateral direction 215 so that the needle 34 positively translates in a lateral direction 215.

Figure 23A:
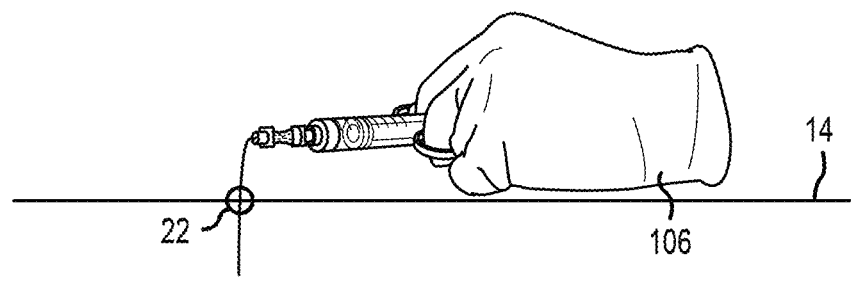
FIGS. 23A-C depict various movements of aspects of a precision steerable and angled medication delivery system including angular motion in a pitch direction.
Figure 23B:
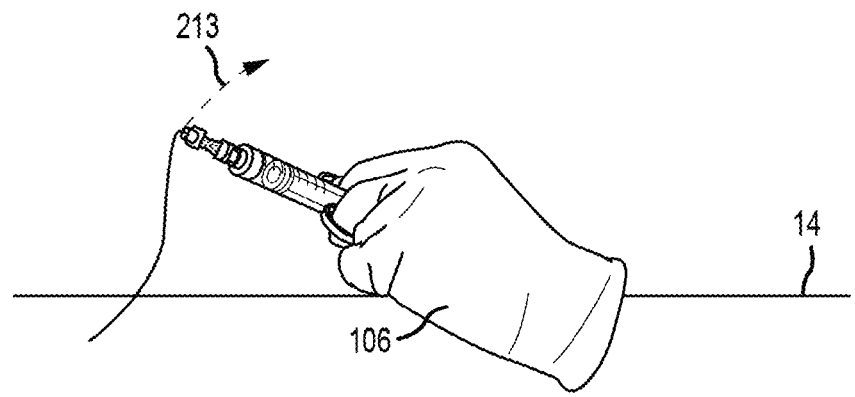
Figure 23C:
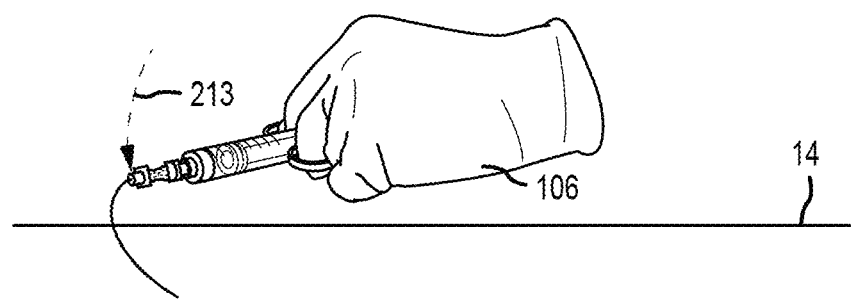

With reference to FIGS. 23A-C, a wrist is anchored at a fixed point 106. As in FIG. 23A, the user manipulates the user's fingers to cause a control syringe 4 to negatively translate in an elevation direction 223, the needle 34 also negatively translating in an elevation direction 223 and penetrate the skin at entry point 22. As in FIGS. 23B-C, the user manipulates the user's fingers to cause a control syringe 4 to positively move in a pitch direction 213 relative to the fixed point 106 and consequently the needle 34 moves in a related pitch direction 213. As one can see, the arcuate motion can be decomposed into vector components as well, with the needle 34 following a curved path but the tip of the needle 34 ultimately moving consistent with the translation vectors as if the needle 34 were translated thusly but along a curved path similar to the pitch direction 213.

Figures 24A, 24B:
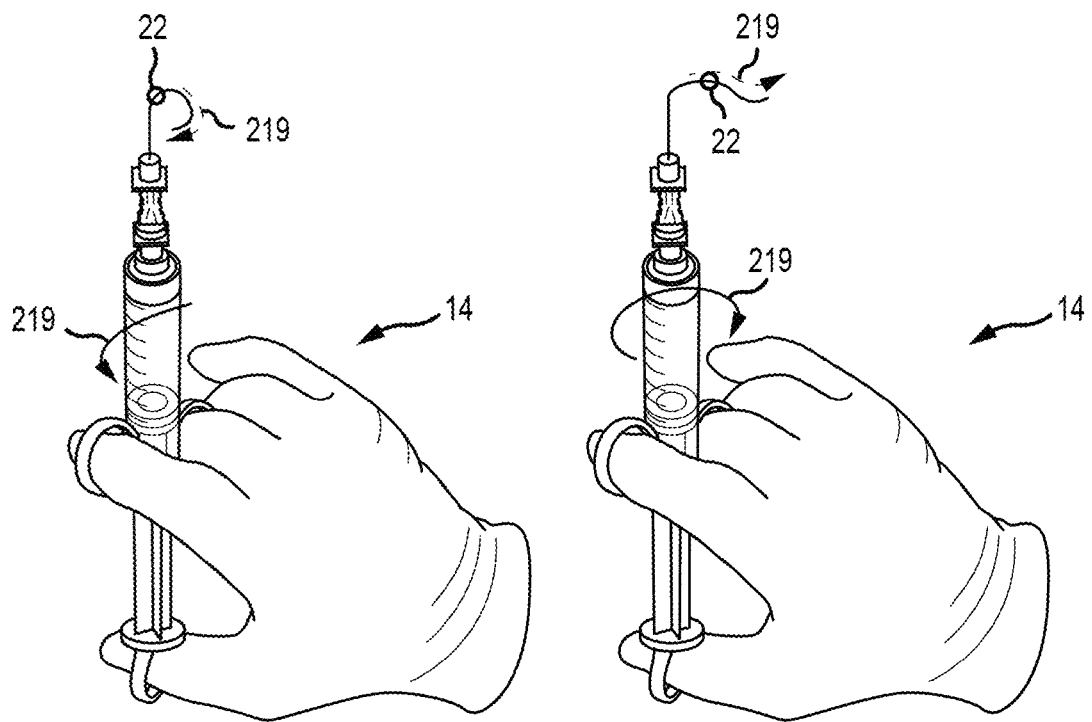
FIGS. 24A-B depict various movements of aspects of a precision steerable and angled medication delivery system including angular motion in a longitudinal axial roll direction.

With reference to FIG. 24A, a wrist is anchored at a fixed point 106. The user manipulates the user's fingers to cause a control syringe 4 to positively rotate in a longitudinal axial roll direction 219 and the needle 34 correspondingly travels in a reciprocal negative axial roll direction 219 relatively about the entry point 22. With reference to FIG. 24B, a wrist is anchored at a fixed point 106. The user manipulates the user's fingers to cause a control syringe 4 to negatively rotate in a longitudinal axial roll direction 219 and the needle 34 correspondingly travels in a reciprocal positive axial roll direction 219 relatively about the entry point 22.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms. In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In addition, the foregoing describes some embodiments of the disclosure, and alterations, modifications, additions and/or changes can be made thereto without departing from the scope and spirit of the disclosed embodiments, the embodiments being illustrative and not restrictive. The disclosure is not to be limited to the illustrated implementations, but on the contrary, is intended to cover various modifications and equivalent arrangements included within the spirit and scope of the disclosure. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. A method of directionally controlled medication delivery using a precision steerable and angled medication delivery system, the method comprising:
    inserting a flexible needle into a patient's soft tissue at an entry point;
    guiding the flexible needle around an obstacle and through intervening soft tissue along a curved path to a delivery site; and
    delivering a medication from the flexible needle to the delivery site,
    wherein the precision steerable and angled medication delivery system includes a bent connector body with a first end and a second end, the first end and the second end being opposite ends of the bent connector body;
    a control syringe in fluid communication with the bent connector body adjacent the first end of the bent connector body, the control syringe comprising:
        a syringe body having a reservoir for medication and a grip, wherein the grip includes a first member and a second member disposed on opposite sides of the syringe body to each receive a finger;
        a plunger insertable into the reservoir to expel the medication, wherein the plunger comprises an at least partial ring configured to receive a user's thumb;
    wherein the second end of the bent connector body is configured to couple to the flexible needle that has a length of at least about 1.5 inches to about 6 inches,
    wherein the first end of the bent connector body has a first longitudinal axis aligned with a syringe longitudinal axis of the control syringe, wherein the second end of the bent connector body has a second longitudinal axis and is configured to align the flexible needle along the second longitudinal axis, wherein the bent connector body is bent so that a fixed bend angle is measured between the first longitudinal axis and the second longitudinal axis, wherein the fixed bend angle is at least about 70 degrees, wherein when the second end of the bent connector body is coupled to the flexible needle, the flexible needle is configured to be steerable within the soft tissue of a body along the curved path in the soft tissue in response to rotation of the bent connector body about the first longitudinal axis, and wherein the bent connector body comprises a channel defined through the bent connector body and connecting the reservoir of the control syringe in fluidic communication to the second end of the bent connector body.

2. The method of claim 1, wherein the fixed bend angle is about 90 degrees.

3. The method of claim 1, wherein the fixed bend angle is about 80 degrees to about 100 degrees.

4. The method of claim 1, wherein the syringe body and the bent connector body are connectable to one another.

5. The method of claim 4, wherein the syringe body and the bent connector body are integrally formed.

6. The method of claim 1, wherein the syringe body and the bent connector body are connectively coupled to one another.

7. The method of claim 1, wherein the flexible needle is a flexible straight needle.

8. The method of claim 1, wherein the bent connector body is an interface between the syringe body and the flexible needle.

9. The method of claim 1, wherein the flexible needle is configured to be curved.

10. The method of claim 1, wherein the flexible needle is configured to be bent.

11. The method of claim 1, wherein the bent connector body and the flexible needle are permanently affixed to one another.

12. The method of claim 1, wherein the bent connector body and the flexible needle are attachable to one another.

13. The method of claim 1, wherein the first member and the second member of the grip of the syringe body are ring apertures that comprise an annulus defining an aperture for receiving a finger therein.

14. The method of claim 1, wherein guiding the flexible needle includes providing positive pressure on the plunger of the control syringe to prevent the flexible needle from clogging during use.

15. A method of directionally controlled medication delivery using a precision steerable and angled medication delivery system, the method comprising:
 inserting a flexible needle into a patient's soft tissue at an entry point;
 guiding the flexible needle around an obstacle and through intervening soft tissue along a curved path to a delivery site; and
 delivering a medication from the flexible needle to the delivery site,
 wherein the precision steerable and angled medication delivery system includes:
  an angled connector body with a first end and a second end; and
  a control syringe having a first end and a second end and a longitudinal axis defined between the first end and the second end, the control syringe comprising:
   a syringe body having a reservoir for medication and a grip, wherein the grip includes a first member and a second member disposed on opposite sides of the syringe body to each receive a finger; and
   a plunger insertable into the reservoir to expel the medication;
 wherein the second end of the angled connector body is configured to couple to the flexible needle that has a length of at least about 1.5 inches to about 6 inches,
 wherein the angled connector body comprises a channel defined through the angled connector body and connecting the reservoir of the control syringe in fluid communication to the flexible needle;
 wherein the second end of the angled connector body has a second longitudinal axis and is configured to align at least a portion of the flexible needle along the second longitudinal axis, such that a fixed bend angle is measured between the longitudinal axis of the control syringe and the second longitudinal axis,
 wherein the fixed bend angle is at least about 70 degrees, and
 wherein, when the second end of the angled connector body is coupled to the flexible needle, the flexible needle is configured to be steerable within the soft tissue of a body along the curved path in the soft tissue in response to rotation of the control syringe about the longitudinal axis of the control syringe.

16. The method of claim 15, wherein the fixed bend angle is about 90 degrees.

17. The method of claim 15, wherein the fixed bend angle is about 80 degrees to about 100 degrees.

18. The method of claim 15, wherein the syringe body and the bent connector body are connectable to one another.

19. The method of claim 18, wherein the syringe body and the angled connector body are integrally formed.

20. The method of claim 15, wherein the syringe body and the angled connector body are connectively coupled to one another.

21. The method of claim 15, wherein the flexible needle is a flexible straight needle.

22. The method of claim 15, wherein the angled connector body is an interface between the syringe body and the flexible needle.

23. The method of claim 15, wherein the flexible needle is configured to be curved.

24. The method of claim 15, wherein the flexible needle is configured to be bent.

25. The method of claim 15, wherein the angled connector body and the flexible needle are permanently affixed to one another.

26. The method of claim 15, wherein the bent connector body and the flexible needle are attachable to one another.

27. The method of claim 15, wherein the first member and the second member of the grip of the syringe body are ring apertures that comprise an annulus defining an aperture for receiving a finger therein.

28. The method of claim 15, wherein guiding the flexible needle includes providing positive pressure on the plunger of the control syringe to prevent the flexible needle from clogging during use.

29. A method of directionally controlled medication delivery using a precision steerable and angled medication delivery system, the method comprising:

inserting a flexible needle into a patient's soft tissue at an entry point;
guiding the flexible needle along a curved path through intervening soft tissue to a delivery site; and
delivering a medication from the flexible needle to the delivery site,
wherein the precision steerable and angled medication delivery system includes:
   a control syringe comprising a syringe body generally aligned along a first longitudinal axis and having a first end and a second end, and a bent portion having a first end and a second end and a second longitudinal axis that generally extends from the second end of the bent portion, wherein the first end of the bent portion is positioned adjacent the second end of the syringe body and the bent portion is in fluid communication with the syringe body,
   the flexible needle having a first end and a second end, and a length between the first end of the flexible needle and the second end of the flexible needle that is between about 1.5 inches and about 6 inches, wherein the first end of the flexible needle is positioned adjacent the second end of the bent portion generally along the second longitudinal axis and is in fluid communication with the second end of the bent portion of the control syringe,
   wherein the second longitudinal axis generally extends from the second end of the bent portion and is angled relative to the first longitudinal axis of the syringe body such that the second longitudinal axis and the first longitudinal axis of the syringe body define a bend angle that is at least about 70 degrees,
   wherein the second end of the bent portion and the first end of the flexible needle are configured to position the flexible needle at the bend angle relative to the first longitudinal axis of the syringe body to facilitate an injection of the medication through the flexible needle along the curved path in the soft tissue to the delivery site, and
   wherein the flexible needle is configured to be steerable when being inserted within a body in a soft tissue along the curved path in the soft tissue in response to rotation of the syringe body of the control syringe about the first longitudinal axis.

30. The method of claim 29, wherein the bend angle is about 90 degrees.

31. The method of claim 29, wherein the bend angle is about 80 degrees to about 100 degrees.

32. The method of claim 29, wherein the syringe body and the bent portion are integrally formed.

33. The method of claim 29, wherein the syringe body and the bent portion are connectable to one another.

34. The method of claim 29, wherein the flexible needle is a flexible straight needle.

35. The method of claim 29, wherein the angled connector body is an interface between the syringe body and the flexible needle.

36. The method of claim 29, wherein the flexible needle is configured to be curved.

37. The method of claim 29, wherein the flexible needle is a configured to be bent.

38. The method of claim 37, wherein the bend of the flexible bent needle is adjacent the second end of the bent portion.

39. The method of claim 29, wherein the second end of the bent portion and the flexible needle are permanently affixed to one another.

40. The method of claim 29, wherein the second end of the bent portion and the flexible needle are attachable to one another.

* * * * *